US012606538B2

(12) United States Patent
Li et al.

(10) Patent No.: US 12,606,538 B2
(45) Date of Patent: Apr. 21, 2026

(54) BENZO[B]SELENOPHENE STING REGULATOR, PREPARATION METHOD AND USE THEREOF

(71) Applicant: CHINA PHARMACEUTICAL UNIVERSITY, Jiangsu (CN)

(72) Inventors: Zhiyu Li, Nanjing (CN); Jinlei Bian, Nanjing (CN); Xi Feng, Nanjing (CN); Dongyu Liu, Nanjing (CN); Zhe Wang, Nanjing (CN); Zhiyu Qian, Nanjing (CN)

(73) Assignee: CHINA PHARMACEUTICAL UNIVERSITY, Nanjing (CN)

( * ) Notice: Subject to any disclaimer, the term of this patent is extended or adjusted under 35 U.S.C. 154(b) by 465 days.

(21) Appl. No.: 18/027,843

(22) PCT Filed: Apr. 18, 2022

(86) PCT No.: PCT/CN2022/087398

§ 371 (c)(1),
(2) Date: Mar. 22, 2023

(87) PCT Pub. No.: WO2023/005267

PCT Pub. Date: Feb. 2, 2023

(65) Prior Publication Data

US 2024/0051934 A1 Feb. 15, 2024

(30) Foreign Application Priority Data

Jul. 27, 2021 (CN) ......................... 202110850842.6

(51) Int. Cl.
*C07D 345/00* (2006.01)
*A61P 35/00* (2006.01)

(52) U.S. Cl.
CPC ............ *C07D 345/00* (2013.01); *A61P 35/00* (2018.01)

(58) Field of Classification Search
None
See application file for complete search history.

(56) References Cited

FOREIGN PATENT DOCUMENTS

| | | | |
|---|---|---|---|
| CN | 103906742 | A | 7/2014 |
| CN | 110036001 | A | 7/2019 |
| CN | 111499617 | A | 8/2020 |
| CN | 113429387 | A | 9/2021 |

OTHER PUBLICATIONS

Van Coppenolle and Renson (Comptes Rendus des Seances de l'Academie des Sciences, Serie C: Sciences Chimiques (1975), 280(5), 283-6) (Year: 1975).*
CAS RN 55473-42-2, CAPLUS (Year: 1975).*
Mhetre et al. (Org. Biomol. Chem., 2017, 15, 1198â1208) (Year: 2017).*
Patani and LaVoie (âBioisosterism: A Rational Approach in Drug Designâ Chem. Rev. 1996, 96, 3147-3176) (Year: 1996).*
Jul. 8, 2022 International Search Report issued in International Patent Application No. PCT/CN2022/087398. Document not uploaded into DAV (internal issue—email sent to Case Resolution on Jul. 24, 2025.) Dec. 3, 2025: Document now reviewed.
Bo-Sheng Pan et al.; "An orally available non-nucleotide STING agonist with antitumor activity"; Science; Aug. 2020; vol. 369; No. 935; pp. 1-12.
Pavel Arsenyan et al.; "Synthesis, structure and cytotoxicity of 3-C, N, S, Se substituted benzo[b] selenophene derivaties"; European Journal of Medicinal Chemistry; 2011; vol. 46; pp. 3434-3443.
Yu Jia Tan et al.; "Amide-Amine Replacement in Indole-2-carboxamides Yields Potent Mycobactericidal Agents with Improved Water Solubility"; American Chemical Society Medicinal Chemistry Letters; 2020; pp. A-I.

* cited by examiner

*Primary Examiner* — Sarah Pihonak
*Assistant Examiner* — Donna M Nestor
(74) *Attorney, Agent, or Firm* — Oliff PLC

(57) ABSTRACT

A benzo[b]selenophene STING regulator, a preparation method therefore and use thereof are disclosed. The structure of the compound is shown in Formula I. A derivative, salt, stereoisomer, prodrug molecule and pharmaceutical composition of the present invention can serve as an immune regulator to effectively activate an innate immune regulation passageway to kill tumor cells.

(I)

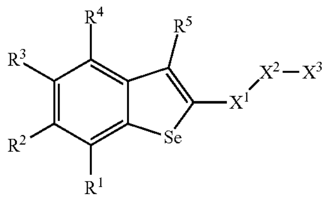

6 Claims, No Drawings

BENZO[B]SELENOPHENE STING REGULATOR, PREPARATION METHOD AND USE THEREOF

TECHNICAL FIELD

The present invention relates to the field of pharmaceuticals, in particular to a benzo[b]selenophene derivative, a pharmaceutically acceptable salt thereof, and a medical application.

BACKGROUND

Cancer immunotherapy treats cancer by invoking the body's own immune system to attack and remove tumor cells. The emergence of immunotherapy has provided excellent therapeutic results and entirely new research ideas for curing tumors, and was named the most important scientific breakthrough of 2013 by the journal *Science* (*Science.* 2015, 348, 56-61). Immune check point blockade therapy and chimeric antigen receptor T cell therapy offer powerful therapeutic means for cancer patients and have received widespread attention (*Drug Discov Today.* 2020, 25, 230-237).

In recent years, the cGAS-STING pathway has been recognized as an important potential target for tumor immunotherapy. Firstly, the cGAS-STING pathway belongs to pattern recognition receptors, which are an important part of innate immune regulation in vivo (*Nature.* 2016, 535, 65-74). It plays a role in immune response by capturing and recognizing abnormal cytoplasmic DNA to activate downstream signaling pathways and regulate the expression of type I interferon. This signaling pathway is initiated by activation of cyclic GMP-AMP synthase. cGAS is an intracellular DNA receptor, which can induce allosteric cGAS proteins by binding to cytoplasmic DNA and catalyze the synthesis of cyclic guanosine monophosphate (2'-3' cGAMP) from ATP and GTP rings (*Nat. Immunol.* 2016, 17, 1142-1149). cGAMP as a second messenger binds to the endoplasmic reticulum receptor stimulator of interferon genes (STING) and activates STING Subsequently, the STING receptor protein undergoes a series of allosterism and displacement, and ultimately recruits TBK1 kinase on golgiosome, which phosphorylates the downstream cytokine IRF3 and NF-κB (*Curr. Opin. Cell Biol.* 2019, 59, 1-7). Phosphorylated cytokines can enter the nucleus to regulate the expression of downstream type I interferon genes and the secretion of type I interferon, which in turn regulates the immune response (*Nature.* 2019, 567, 394-398).

The cGAS-STING pathway as an important regulation passageway of the immune response in vivo is closely associated with many diseases. In previous studies, excessive activation of the cGAS-STING pathway was considered as one of the triggers of a variety of chronic inflammation and autoimmune diseases (*Cell Mol. Immunol.* 2019, 16, 236-241). However, agitation of this pathway, on the other hand, is considered as an important target for tumor immunotherapy based on the strong regulation ability of cGAS-STING on the immune response (*J. Hematol. Oncol.* 2019, 12, 35). In the cGAS-STING pathway, the transmembrane receptor STING is the most critical node in regulating the pathway. Therefore, the development of a new generation of drugs that can agitate the STING receptor plays an important role in enhancing the efficacy of existing tumor immunotherapy. In preclinical mouse tumor models, STING agonists show high antitumor activity that can completely inhibited tumor growth and completely remove tumors (*Nature.* 2018, 564, 439-443; *Science.* 2020, 369, eaba6098; *Science.* 2020, 369, 993-999).

So far, STING agonists have been developed by a number of pharmaceutical companies, including ADU-S100 from Novartis, MK-1454 from Merck, etc., and many of the STING agonists successively entered clinical trials. Clinical development of the STING agonists is currently in its infancy, and people hope to develop a new generation of efficient and low-toxicity STING regulator that exhibits excellent effect and function as well as good pharmacokinetic absorption activity.

SUMMARY

The present invention aims to search for an anti-tumor candidate compound having a novel structure, high activity, small side effect and good drug metabolism properties. These compounds are used alone or in combination with other antitumor drugs, thus improving the efficacy of existing antitumor drugs and reducing dose and toxicity.

Disclosed in the present invention are a compound of general formula (I), a stereisomer or a pharmaceutically acceptable salt thereof.

Disclosed in the present are a compound of general formula (I), a steroisomer or a pharmaceutically acceptable salt thereof.

(I)

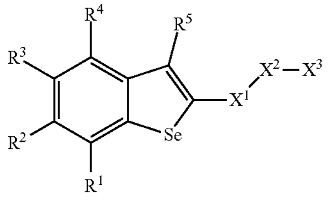

Where $R^1$ is selected from H, halo, cyano, nitro, $OR^6$, $N(R^6)_2$, $C_1$-$C_6$ alkyl, $C_1$-$C_6$ haloalkyl, $C_1$-$C_6$ alkyl substituted with $OR^6$ or $C_1$-$C_6$ alkyl substituted with $N(R^6)_2$;

$R^2$ is selected from H, halo, cyano, nitro, $OR^6$, $SR^6$, $N(R^6)_2$, $COOR^6$, $C(O)N(R^6)_2$, $C_1$-$C_6$ alkyl, $C_1$-$C_6$ haloalkyl, $C_1$-$C_6$ alkyl substituted with $OR^6$, $C_1$-$C_6$ alkyl substituted with $N(R^6)_2$, $C_2$-$C_6$ alkenyl, $C_2$-$C_6$ haloalkenyl, $C_2$-$C_6$ alkynyl, $C_2$-$C_6$ haloalkynyl(enyl) or $C_3$-$C_6$ cycloalkyl;

$R^3$ is selected from H, halo, cyano, nitro, $OR^6$, $SR^6$, $N(R^6)_2$, $COOR^6$, $C(O)N(R^6)_2$, $C_1$-$C_6$ alkyl, $C_1$-$C_6$ haloalkyl, $C_1$-$C_6$ alkyl substituted with $OR^6$, $C_1$-$C_6$ alkyl substituted with $N(R^6)_2$, $C_2$-$C_6$ alkenyl, $C_2$-$C_6$ haloalkenyl, $C_2$-$C_6$ alkynyl, $C_2$-$C_6$ haloalkynyl(enyl) or $C_3$-$C_6$ cycloalkyl;

or $R^2$ and $R^3$, together with atoms to which they are attached, form a 5- or 6-membered heterocycle including one to two members selected from O, S or N ring members.

$R^4$ is selected from H, halo, cyano, nitro, $OR^6$, $N(R^6)_2$, $C_1$-$C_6$ alkyl, $C_1$-$C_6$ haloalkyl, $C_1$-$C_6$ alkyl substituted with $OR^6$ or $C_1$-$C_6$ alkyl substituted with $N(R^6)_2$;

$R^5$ is selected from H, halo, cyano, $C_1$-$C_6$ alkyl, $C_1$-$C_6$ haloalkyl and $C_3$-$C_6$ cycloalkyl;

$R^6$ on the same atom is identical or different, $R^6$ on different atoms are identical or different, and each $R^6$ is independently selected from H, $C_1$-$C_6$ alkyl, $C_1$-$C_6$ haloalkyl, $C_3$-$C_6$ cycloalkyl, $C_3$-$C_8$ heterocyclyl or $C_5$-$C_{10}$ aryl;

$X^1$ is C(O);

$X^2$ is $(C(R^7)_2)_{(1-3)}$;

$R^7$ on the same atom is identical or different, $R^7$ on different atoms are identical or different, and each $R^7$ is independently selected from H, halo, CN, $OR^6$, $N(R^6)_2$, $C_1$-$C_6$ alkyl, $C_1$-$C_6$ haloalkyl, $C_1$-$C_6$ alkyl substituted with $OR^6$ or $C_3$-$C_6$ cycloalkyl;

or two $R^7$ on different carbon atoms, together with atoms to which they are attached, can form a 3- to 6-membered ring;

or two $R^7$ on a single carbon atom, together with atoms to which they are attached, can form a 3- to 6-membered ring; and $X^3$ is selected from $COOR^6$, $C(O)N(R^6)_2$, C(O)NHOH, $SO_2R^6$, $S(O)NR^6$ or $C(CF_3)_2OR^6$.

In a preferable embodiment of the present invention, where $R^1$ is selected from H, F, $C_1$-$C_3$ alkyl or $C_1$-$C_3$ haloalkyl, preferably H and F;

$R^2$ is selected from H, halo, $C_1$-$C_3$ alkyl, $C_1$-$C_3$ haloalkyl, $OC_1$-$C_3$ alkyl, $OC_1$-$C_3$ haloalkyl or —OH, preferably H, F, Cl, $CH_3$, $CH_2CH_3$, $OCH_3$, $OCH_2CH_3$, $OCH(CH_3)_2$ or $OCHF_2$;

$R^3$ is selected from H, halo, $C_1$-$C_3$ alkyl, $C_1$-$C_3$ haloalkyl, $OC_1$-$C_3$ alkyl, $OC_1$-$C_3$ haloalkyl or —OH, preferably H, —OH, F, Cl, $CH_3$, $CH_2CH_3$, $OCH_3$, $OCH_2CH_3$, $OCH(CH_3)_2$ or $OCHF_2$;

$R^4$ is selected from H, F, $C_1$-$C_3$ alkyl or $C_1$-$C_3$ haloalkyl, preferably H and F;

$R^5$ is selected from H, halo, $C_1$-$C_3$ alkyl or $C_1$-$C_3$ haloalkyl, preferably H.

$X^1$ is C(O);

$X^2$ is $CH_2CHR^7$;

X3 is selected from $COOR^6$, $C(O)N(R^6)_2$, C(O)NHOH, $SO_2R^6$, $S(O)NR^6$ or $C(CF_3)_2OR^6$, preferably, COOH, $COOCH_3$, $COOCH_2CH_3$ and C(O)NHOH;

Each $R^6$ is independently selected from H, $C_1$-$C_3$ alkyl, $C_1$-$C_3$ haloalkyl, $C_3$-$C_6$ cycloalkyl, $C_3$-$C_8$ heterocyclyl or $C_5$-$C_{10}$ aryl;

Each $R^7$ is independently selected from H, F, $C_1$-$C_4$ alkyl, $C_1$-$C_4$ haloalkyl, $C_3$-$C_6$ cycloalkyl or $C_1$-$C_4$ alkyl substituted with $OC_1$-$C_3$, preferably H, $CH_3$, $CH_2CH_3$, $CH_2CH_2CH_3$, $CH(CH_3)_2$, $CH_2OCH_3$ or cyclopropyl.

In a second preferable embodiment of the present invention, where $R^1$ is selected from H, F, $C_1$-$C_3$ alkyl or $C_1$-$C_3$ haloalkyl, preferably H and F;

$R^2$ is selected from H, halo, $C_1$-$C_3$ alkyl, $C_1$-$C_3$ haloalkyl, $OC_1$-$C_3$ alkyl, $OC_1$-$C_3$ haloalkyl or —OH, preferably F, Cl, $CH_3$, $CH_2CH_3$, $OCH_3$, $OCH_2CH_3$, $OCH(CH_3)_2$ or $OCHF_2$;

$R^3$ is selected from H, halo, $C_1$-$C_3$ alkyl, $C_1$-$C_3$ haloalkyl, $OC_1$-$C_3$ alkyl, $OC_1$-$C_3$ haloalkyl or —OH, preferably F, Cl, $CH_3$, $CH_2CH_3$, $OCH_3$, $OCH_2CH_3$, $OCH(CH_3)_2$ or $OCHF_2$;

$R^4$ is selected from H, F, $C_1$-$C_3$ alkyl or $C_1$-$C_3$ haloalkyl, preferably H and F;

$R^5$ is selected from H, halo, $C_1$-$C_3$ alkyl or $C_1$-$C_3$ haloalkyl, preferably H.

$X^1$ is C(O);

$X^2$ is $CHR^7CHR^7$;

X3 is selected from $COOR^6$, $C(O)N(R^6)_2$, C(O)NHOH, $SO_2R^6$, $S(O)NR^6$ or $C(CF_3)_2OR^6$; preferably, COOH, $COOCH_3$, $COOCH_2CH_3$ and C(O)NHOH;

Each $R^6$ is independently selected from H, $C_1$-$C_3$ alkyl, $C_1$-$C_3$ haloalkyl, $C_3$-$C_6$ cycloalkyl, $C_3$-$C_8$ heterocyclyl or $C_5$-$C_{10}$ aryl;

Each $R^7$ is independently selected from H, F, $C_1$-$C_4$ alkyl, $C_1$-$C_4$ haloalkyl, $C_3$-$C_6$ cycloalkyl or $C_1$-$C_4$ alkyl substituted with $OC_1$-$C_3$, or two $R^7$, together with atoms to which they are attached, form a 3- to 6-membered ring.

In some specific instances, $R^1$, $R^4$ and $R^5$ are all hydrogen atoms.

In some specific instances, also provided in the present invention is a compound as shown in Formula I-1:

(I-1)

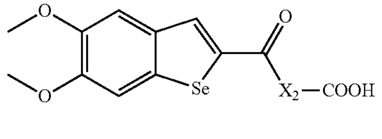

where $X^2$ is $CHR^7CHR^7$;

$R^7$ is identical or different, and each $R^7$ is independently selected from H, halo, CN, $C_1$-$C_6$ alkyl, $C_1$-$C_6$ haloalkyl, $C_1$-$C_6$ alkyl substituted with $OR^6$ and $C_3$-$C_6$ cycloalkyl; or two $R^7$ on different carbon atoms, together with atoms to which they are attached, form a 3- to 6-membered ring; and $R^6$ is independently selected from H, $C_1$-$C_3$ alkyl, $C_1$-$C_3$ haloalkyl, $C_3$-$C_6$ cycloalkyl, $C_3$-$C_5$ heterocyclyl or $C_5$-$C_{10}$ aryl.

The pharmaceutically acceptable salt of the compound of general formula (I) of the present invention refers to a salt that is prepared from the compound of general formula (I) and a pharmaceutically acceptable non-toxic base including an inorganic base or an organic base. The salt prepared from the inorganic base includes an aluminium salt, an ammonium salt, a calcium salt, a lithium salt, a magnesium salt, a potassium salt, a sodium salt, a zinc salt, etc. Particularly preferred are the ammonium salt, the calcium salt, the magnesium salt, the potassium salt and the sodium salt. The salt prepared from the pharmaceutically acceptable organic non-toxic base including primary amine, secondary amine and tertiary amine. Substituted amines include natural substituted amines, cyclic amines and basic anion exchange resins, e.g. betaine, caffeine, choline, N-ethylpiperidine, N, N'-dibenzylethylenediamine, diethylamine, 2-dimethylaminoethanol, arginine, ethanolamine, ethylenediamine, N-ethylmorpholine, glucosamine, methyl glucosamine, 2-diethylaminoethanol, glucosamine, histidine, aminoethanol, hydroxocobalamin, lysine, morpholine, piperazine, piperidine, piperidine, polyamine resins, triethylamine, trimethylamine, tripropylamine, isopropylamine, trometamol, etc.

Also provided in the present invention is a specific compound as shown in any one of structural formulas or a pharmaceutically acceptable salt thereof.

| Code | Structural formula |
| --- | --- |
| I-1 | 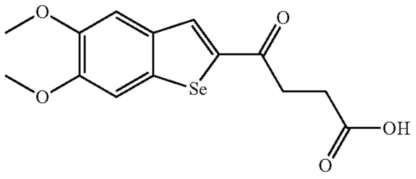 [SMILES: COc1cc2cc(C(=O)CCC(=O)O)[se]c2cc1OC] |

-continued
| Code | Structural formula |
|---|---|
| I-2 | 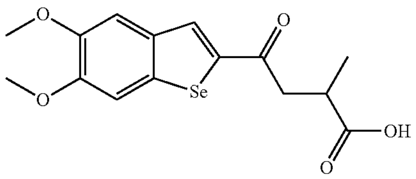 [SMILES: COc1cc2cc(C(=O)CC(C)C(=O)O)[se]c2cc1OC] |
| I-3 | 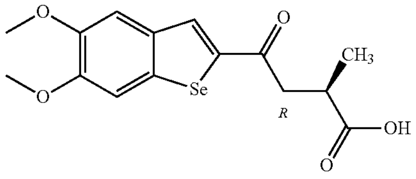 |
| I-4 | 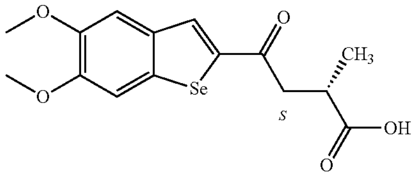 |
| I-5 | 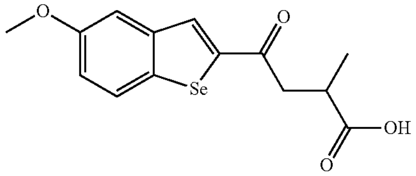 [SMILES: COc1ccc2[se]c(C(=O)CC(C)C(=O)O)cc2c1] |
| I-6 | 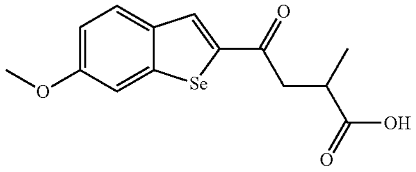 [SMILES: COc1ccc2cc(C(=O)CC(C)C(=O)O)[se]c2c1] |
| I-7 | 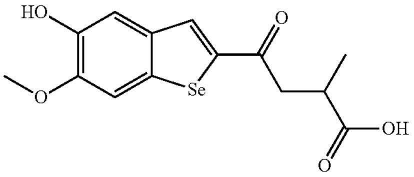 [SMILES: COc1cc2[se]c(C(=O)CC(C)C(=O)O)cc2cc1O] |
| I-8 | 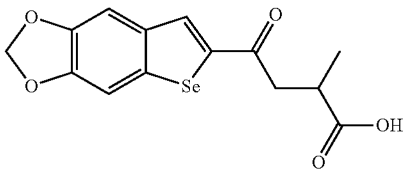 [SMILES: CC(CC(=O)c1cc2cc3c(cc2[se]1)OCO3)C(=O)O] |
| I-9 | 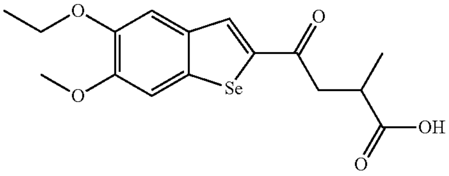 [SMILES: CCOc1cc2cc(C(=O)CC(C)C(=O)O)[se]c2cc1OC] |
-continued
| Code | Structural formula |
|---|---|
| I-10 | 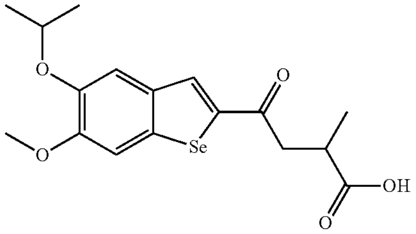 [SMILES: COc1cc2[se]c(C(=O)CC(C)C(=O)O)cc2cc1OC(C)C] |
| I-11 | 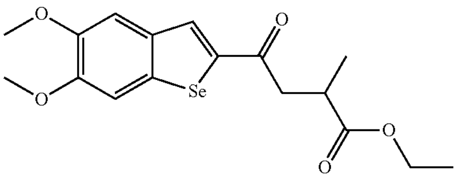 [SMILES: CCOC(=O)C(C)CC(=O)c1cc2cc(OC)c(OC)cc2[se]1] |
| I-12 | 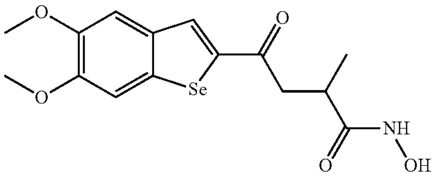 [SMILES: COc1cc2cc(C(=O)CC(C)C(=O)NO)[se]c2cc1OC] |
| I-13 | 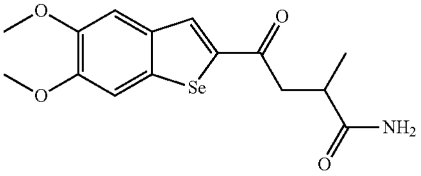 [SMILES: COc1cc2cc(C(=O)CC(C)C(N)=O)[se]c2cc1OC] |
| I-14 | 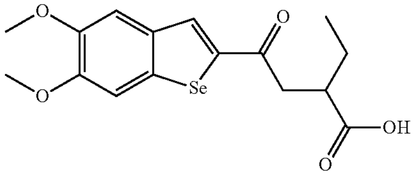 [SMILES: CCC(CC(=O)c1cc2cc(OC)c(OC)cc2[se]1)C(=O)O] |
| I-15 | 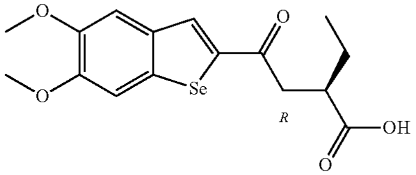 |
| I-16 | 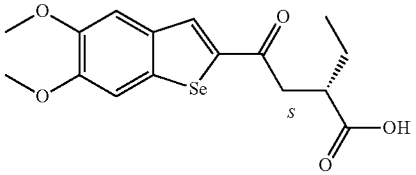 |
| I-17 | 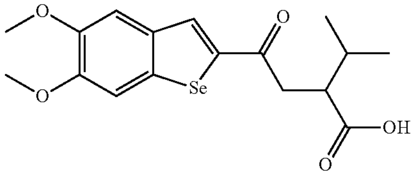 [SMILES: COc1cc2cc(C(=O)CC(C(=O)O)C(C)C)[se]c2cc1OC] |

-continued
| Code | Structural formula |
|---|---|
| I-18 | 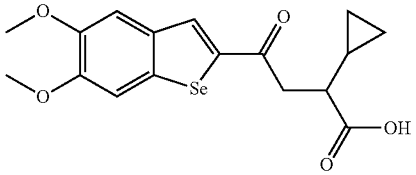 [SMILES: COc1cc2cc(C(=O)CC(C(=O)O)C3CC3)[se]c2cc1OC] |
| I-19 | 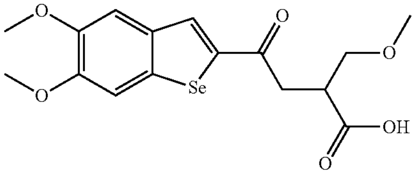 |
| I-20 | 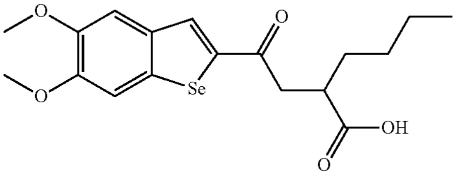 [SMILES: CCCCC(CC(=O)c1cc2cc(OC)c(OC)cc2[se]1)C(=O)O] |
| I-21 | 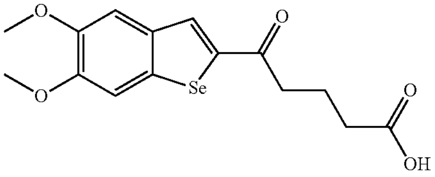 [SMILES: COc1cc2cc(C(=O)CCCC(=O)O)[se]c2cc1OC] |
| I-22 | 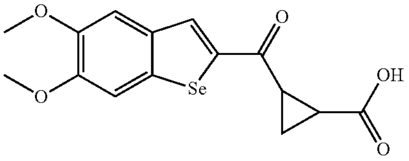 [SMILES: COc1cc2cc(C(=O)C3CC3C(=O)O)[se]c2cc1OC] |
| I-23 | 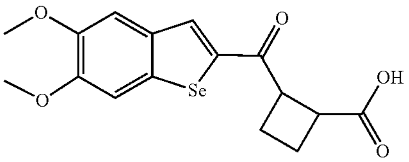 [SMILES: COc1cc2cc(C(=O)C3CCC3C(=O)O)[se]c2cc1OC] |
| I-24 | 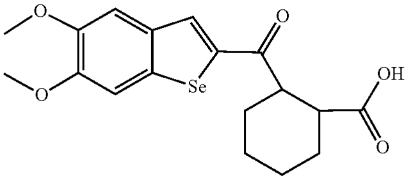 [SMILES: COc1cc2cc(C(=O)C3CCCCC3C(=O)O)[se]c2cc1OC] |
Another objective of the present invention is to provide a preparation method for a compound as shown in general formula (I).
When the compound is a compound as shown in general formula (Ia), the synthetic route of the compound is as follows.
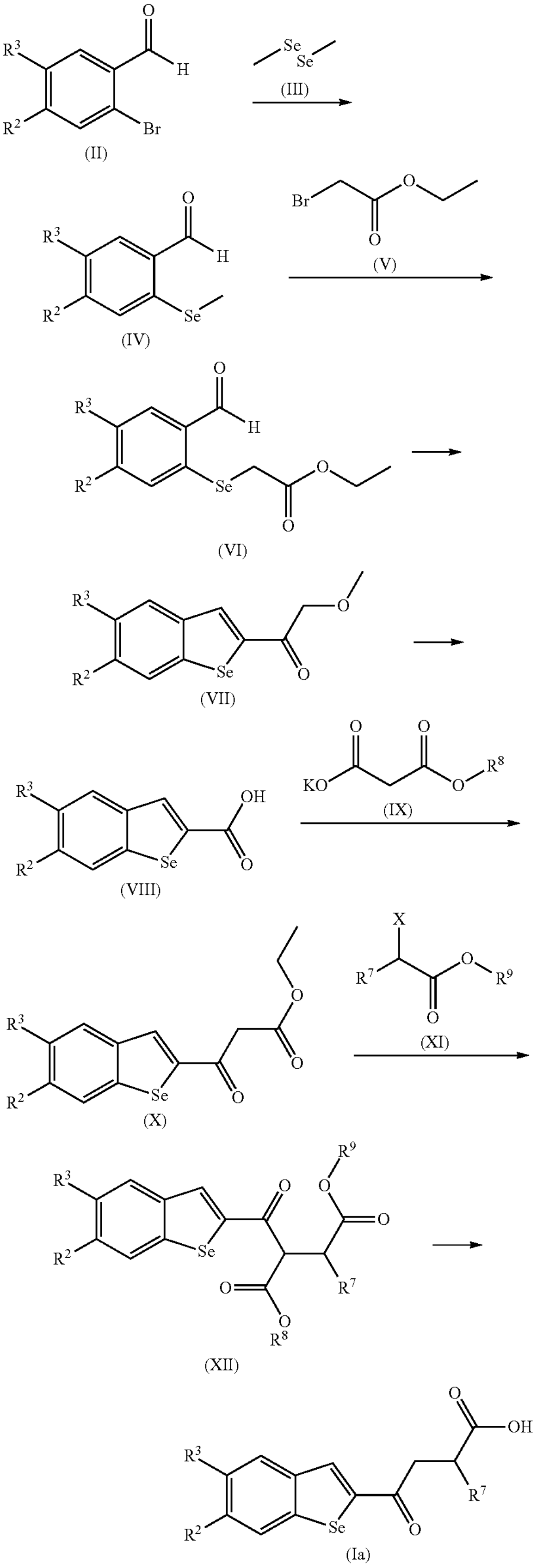

Where $R^2$, $R^3$, and $R^7$ are as described previously, $R^8$ can be $CH_3$, $CH_2CH_3$ and $C(CH_3)_3$, $R^9$ can be $CH_3$ and $CH_2CH_3$, and X can be Cl, Br and I.

In some more specific instances, each of $R^2$ and $R^3$ is independently selected from F, H, $CH_3$, $CH_2CH_3$, $OCH_3$, $OCH_2CH_3$ and $OCH(CH_3)_2$, $R^3$ can be $CH_3$, $CH_2CH_3$ and $C(CH_3)_3$, $R^7$ can be H, $CH_3$, $CH_2CH_3$, $CH_2CH_2CH_3$, $CH(CH_3)_2$, $CH_2OCH_3$ and cyclopropyl, $R^5$ can be $CH_3$ and $CH_2CH_3$, and X can be Cl, Br and I.

In some more specific instances, in the process of preparing a compound (IV) from a compound (II), dimethyldiselenide (III) serves as a reactant, DTT, mercaptoethanol, potassium carbonate and DBU can serve as reaction reagents, and tetrahydrofuran and DMF can serve as solvents.

In some more specific instances, in the process of preparing a compound (VI) from the compound (IV), ethyl 2-bromoacetate (V) serves as a reactant, and DMF can serve as a reaction reagent.

In some more specific instances, in the process of preparing a compound (VII) from the compound (VI), potassium carbonate, sodium carbonate and sodium hydroxide can serve as reaction reagents, and DMF and acetonitrile can serve as solvents.

In some more specific instances, in the process of preparing a compound (VIII) from the compound (VII), potassium carbonate, sodium hydroxide and lithium hydroxide can serve as reaction reagents, and water, methanol and tetrahydrofuran can serve as reaction solvents.

In some more specific instances, in the process of preparing a compound (X) from the compound (VIII), monomethyl potassium malonate (IX) serves as a reactant, CDI and $MgCl_2$ can serve as reaction reagents, and tetrahydrofuran and DMF can serve as reaction solvents.

In some more specific instances, in the process of preparing the compound (XII) from the compound (X), halogenated acid ester (XI) serves as a reactant, potassium carbonate, sodium ethoxide and sodium hydride can serve as reaction reagents, and tetrahydrofuran and DMF can serve as reaction solvents.

In some more specific instances, in the process of preparing a compound of general formula (Ia) from the compound (XII), potassium carbonate, sodium hydroxide and lithium hydroxide can serve as reaction reagents, and hydrochloric acid, acetic acid, water and tetrahydrofuran can serve as reaction solvents.

When the compound is a compound as shown in general formula (Ib), the synthetic route of the compound is as follows.

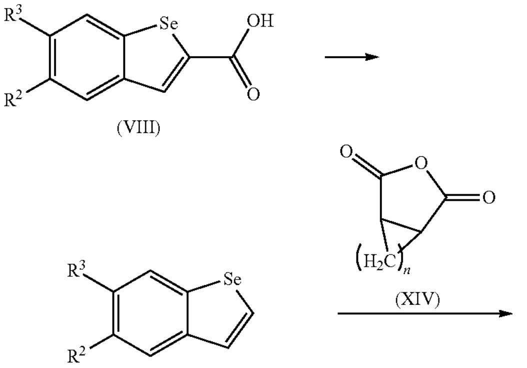

(VIII)

(XIV)

(XIII)

-continued

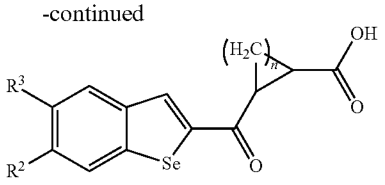

(Ib)

$R^2$ and $R^3$ are as described previously, n representing 1, 2, 3 or 4; and in some more specific instances, each of $R^2$ and $R^3$ is independently selected from F, Cl, $CH_3$, $CH_2CH_3$, $OCH_3$, $OCH_2CH_3$ and $OCH(CH_3)_2$, n representing 1, 2, 3 or 4.

In some more specific instances, in the process of preparing a compound XIII from the compound (VIII), copper powder serves as a reaction reagent, and quinoline serves as a reaction solvent.

In some more specific instances, in the process of preparing a compound of general formula (Ib) from the compound XIII, succinic anhydride (XIV) containing different substituents serves as a reactant, aluminum trichloride, zinc chloride and titanium tetrachloride serve as reaction reagents, and dichloromethane serves as a reaction solvent.

Provided in the present invention is a drug composition, including an active component of an effective dose of drug and a pharmaceutically acceptable accessory; and the active component includes a compound of general formula (I), and one or more of pharmaceutically acceptable salts thereof. In the drug composition, the accessory includes a pharmaceutically acceptable carrier, a diluent and/or an excipient.

The drug composition can be prepared into various types of administration unit dosage forms such as tablets, pills, powders, liquids, suspensions, emulsions, granules, pellets, capsules and injections (solutions or suspensions) depending on the therapeutic purpose, preferably tablets, capsules, liquids, suspensions and injections (solutions or suspensions).

The compound of the present invention can be clinically administered by oral administration, injection and other means.

Also provided in the present invention is a use of the compound as shown in Formula (I), or a pharmaceutically acceptable salt thereof, or a pharmaceutically acceptable drug composition in the preparation of drugs that activate a cGAS-STING pathway.

Also provided in the present invention is a use of the compound as shown in Formula (I), or a pharmaceutically acceptable salt thereof, or a pharmaceutically acceptable drug composition in the preparation of a drug, the drug being used for treating diseases related to the activity of the STING pathway.

Also provided in the present invention is a use of the compound as shown in Formula (I), or a pharmaceutically acceptable salt thereof, or a pharmaceutically acceptable drug composition in the preparation of drugs that treat autoimmune diseases, infectious diseases, cancer and precancerous syndromes. Cancer includes melanoma, colon cancer, breast cancer, lung cancer and squamous cell carcinoma.

Also provided in the present invention is a use of the compound as shown in Formula (I), or a pharmaceutically acceptable salt thereof, or a pharmaceutically acceptable drug composition in the preparation of an immune adjuvant.

Unless otherwise indicated, the following terms used in the description and claims have the meanings discussed below.

The term "alkyl" refers to a monovalent straight or branched chain saturated aliphatic alkyl group that has a designated number of carbon atoms. Alkyl can be substituted or unsubstituted. When alkyl is substituted, there are preferably one or more substituents, more preferably one to three substituents, and most preferably one or two substituents.

The term "alkenyl" refers to a straight chain, branched chain or cyclic group, and a main chain contains a non-aromatic alkyl group with a designated number of carbon atoms and at least one carbon-carbon double bond. Alkenyl includes vinyl, propenyl, butenyl, 2-methylbutenyl, cyclohexenyl, etc. The straight chain, branched chain or cyclic part of alkenyl can contain a double bond, and if it indicates that alkenyl is substituted, this part can be substituted.

The term "alkynyl" refers to a straight chain, branched chain or cyclic group, and a main chain contains a non-aromatic alkyl group with a designated number of carbon atoms and at least one carbon-carbon triple bond. Alkynyl includes acetenyl, propargyl, butynyl, 3-methylbutynyl, etc. The straight chain, branched chain or cyclic part of alkynyl can contain a triple bond, and if it indicates that alkynyl is substituted, this part can be substituted.

The term "halo" represents F, Cl, Br or I, preferably F, Cl and Br.

The term "haloalkyl" refers to alkyl as defined above in which one or more hydrogen atoms have been substituted with halo.

The term "haloalkenyl" refers to alkenyl as defined above in which one or more hydrogen atoms have been substituted with halo.

The term "haloalkynyl" refers to alkynyl as defined above in which one or more hydrogen atoms have been substituted with halo.

The term "cycloalkyl" represents a group of a single ring or fused ring (said "fused" ring means that each ring in the system shares a pair of adjacent carbon atoms with other rings in the system) where all members are carbon, where one or more rings do not have a completely connected π electronic system, and instances of cycloalkyl are (not limited to) cyclopropane, cyclobutane, cyclopentane, cyclopentene, cyclohexane, adamantane, cyclohexadiene, cycloheptane and cycloheptatriene. Cycloalkyl can be substituted or unsubstituted.

The term "fused ring" refers to a cyclic group formed by substituents on different atoms in straight or branched chain alkane, or a cyclic group formed by substituents on different atoms in another ring.

The term "heterocyclyl" represents a saturated cyclic group containing three to eight ring atoms, in which one or two of the ring atoms are heteroatoms selected from N, O or $S(O)_m$ (where m is an integer ranging from 0 to 2), and the rest of the ring atoms are C, in which one or two of the C atoms can be optionally substituted with carbonyl.

The term "aryl" represents an all-carbon monocyclic or fused polycyclic group containing five to ten carbon atoms, and has a completely conjugated π electronic system.

Non-limiting instances of aryl include phenyl, naphthyl and anthryl. Aryl can be substituted or unsubstituted.

The present invention includes all possible isomers, and salts of racemes, enantiomers, diastereoisomers, tautomers and mixture thereof, solvates and solvated salts.

DETAILED DESCRIPTION

To further elaborate on the present invention, a series of embodiments are provided below. These embodiments are entirely illustrative, and are only used for describing the present invention specifically, and should not be understood as a limit of the present invention.

The raw materials and equipment used in the embodiments of the present invention are known products and obtained by purchasing commercially available products.

Abbreviation

DTT DL-Dithiothreitol
DBU 1,8-diazabicyclo[5.4.0]undec-7-ene
$^1$H NMR Proton nuclear magnetic resonance spectrum
$^{13}$C NMR $^{13}$C nuclear magnetic resonance spectrum
HRMS High resolution mass spectrum
DMSO Dimethyl sulfoxide
$CDCl_3$ Deuterated chloroform
TLC Thin-layer chromatography
DMF N,N-dimethylformamide
CDI N,N-carbonyldiimidazole

Embodiment 1

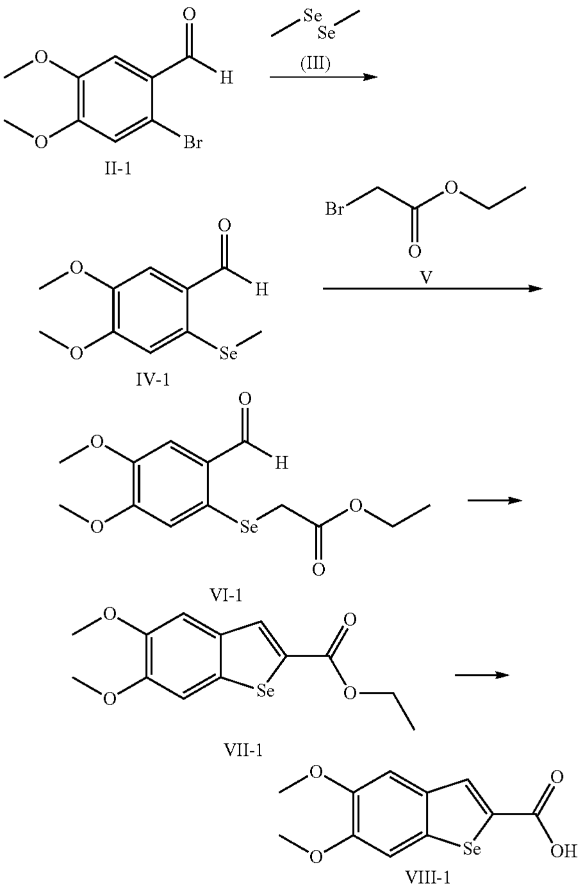

II-1, IV-1, VI-1, VII-1, VIII-1

Step 1: preparation of 4,5-dimethoxy-2-(methylseleno) benzaldehyde (IV-1)

3.14 g of DTT (20.4 mmol), 2.56 g of dimethyldiselane (III, 13.6 mmol) and 50 mL of DMF were added into a 250 mL single mouth flask, and stirred for 1 h at room temperature under nitrogen protection. 5.0 g of 2-Bromo-4,5-dimethoxybenzaldehyde (IT-1) (20.4 mmol) and 7.76 g of DBU (51 mmol) were added into the reaction flask, and stirred overnight at room temperature under nitrogen protection. The reaction was monitored by TLC, and stopped after the reactant II-1 reacted completely. The reaction liquid was poured into 200 mL of ice water, and a solid was precipitated. Suction filtration was carried out, and a filter cake was washed with water and dried to obtain a light yellow solid of 4.46 g with a yield of 84%. $^{1}$H NMR (300 MHz, $CDCl_3$): δ=10.19 (s, 1H), 7.35 (s, 1H), 7.00 (s, 1H), 3.99 (s, 3H), 3.94 (s, 3H), 2.32 (s, 3H) ppm. HRMS ($ESI^+$): $C_{10}H_{13}O_3Se$ $(M+H)^+$, 261.0024; found, 261.0021.

Step 2: preparation of 2-((2-formyl-4,5-dimethoxyphenyl) seleno) ethyl acetate (VI-1)

4.0 g of the compound IV-1 (15.4 mmol) and 8.5 mL of ethyl bromoacetate (77 mmol) were added into a 100 mL single mouth flask, and stirred at 170° C. for 4 h. After it was monitored by TLC that the reactant IV-1 reacted completely, the reaction was stopped. Reaction liquid was cooled to room temperature, added with 30 mL of water for dilution, and extracted twice using 50 mL of ethyl acetate. Organic layers were combined, washed with 50 mL of water, washed with 30 mL of a saturated salt solution and dried with sodium sulphate anhydrous, and underwent suction filtration, and a filtrate was vaporized under reduced pressure to remove a solvent to obtain a brown oily substance, which directly entered into the next step of the reaction without additional purification. HRMS ($ESI^+$): $C_{13}H_{17}O_5Se$ $(M+H)^+$, 333.0236; found, 333.0233.

Step 3: preparation of 5,6-dimethoxybenzo[b]selenophene-2-ethyl formate (VII-1)

The compound VI-1 obtained in the previous step was added into a 100 mL single mouth flask, and 7.6 g of potassium carbonate (55 mmol) and 25 mL of acetonitrile were added. A reflux reaction was carried out for 6 h. After it was detected by TLC that the raw materials reacted completely, heating was stopped. Reaction liquid underwent suction filtration, was vaporized under reduced pressure to remove a solvent, added with 50 mL of water, and extracted twice using 40 mL of ethyl acetate. Organic layers were combined, washed with water, washed with a saturated salt solution and dried with sodium sulphate anhydrous, underwent suction filtration, and were concentrated. A crude product was purified by column chromatography using silica gel to obtain an earthy yellow solid of 3.2 g with a total yield of 46% in two steps. $^{1}$H NMR (300 MHz, $CDCl_3$): δ=8.17 (s, 1H), 7.31 (s, 1H), 7.28 (s, 1H), 4.40 (q, J=7.1 Hz. 2H), 3.97 (s, 3H), 3.94 (s, 3H), 1.41 (t, J=7.1 Hz. 3H) ppm. HRMS ($ESI^+$): calcd for $C_{13}H_{14}O_4Se$ $(M+H)^+$ 315.0130; found, 315.0124.

Step 4: preparation of 5,6-dimethoxybenzo[b]selenophene-2-formic acid (VIII-1)

3.2 g of the compound VII-1, 35 mL of tetrahydrofuran and 35 mL of methanol were added into a 250 mL reaction flask. A total of 15 mL of a 2 N aqueous sodium hydroxide solution was added into the reaction flask at room temperature, and the mixture underwent a stirred reaction at 60° C. for 3 h. After it was detected by TLC that the reaction was completed, reaction liquid was concentrated, pH was adjusted to 3-4 using 1 N hydrochloric acid, and a solid was precipitated. After suction filtration, a filter cake was washed with water and dried to obtain a light yellow solid of 2.9 g with a yield of 98%. $^{1}$H NMR (300 MHz, $CDCl_3$): δ=8.28 (s, 1H), 7.34 (s, 1H), 7.31 (s, 1H), 3.98 (s, 3H), 3.95 (s, 3H) ppm. HRMS ($ESI^-$): $C_{11}H_9O_4Se$ $(M-H)^-$, 284.9672; found, 284.9674.

Embodiment 2

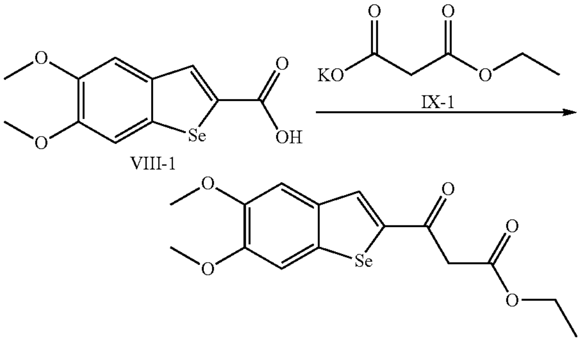
VIII-1
IX-1
X-1

Preparation of 3-(5,6-dimethoxybenzo[b]selenophene-2-yl)-3-oxo-propionic acid ethyl ester (X-1)

2.9 g of the compound VIII-1 (10.1 mmol), 5.1 g of CDI (31.6 mmol) and 50 mL of anhydrous tetrahydrofuran were added into a 100 mL reaction flask, and stirred for 1 h at room temperature. 5.4 g of ethyl potassium malonate (31.6 mmol) and 3.0 g of magnesium chloride (31.6 mmol) were added into the above reaction liquid and continued to be stirred for 4 h at room temperature. After it was detected by TLC that the reaction was completed, the reaction liquid was added with 50 mL of water for dilution, and extracted twice using 40 mL of ethyl acetate. After being combined, organic layers were washed with water, washed with a saturated salt solution and dried with sodium sulphate anhydrous, underwent suction filtration, and were concentrated to obtain a crude product. The crude product was purified by column chromatography using silica gel to obtain a yellow solid of 3.0 g with a yield of 84%. $^{1}$H NMR (300 MHz, $CDCl_3$): δ=8.09 (s, 1H), 7.33 (s, 1H), 7.30 (s, 1H), 4.26 (q, J=7.1 Hz, 2H), 3.98 (s, 5H), 3.94 (s, 3H), 1.30 (t, J=7.1 Hz, 3H) ppm. HRMS ($ESI^+$): $C_{15}H_{17}O_5Se$ $(M+H)^+$, 357.0236; found, 357.0231.

Embodiment 3

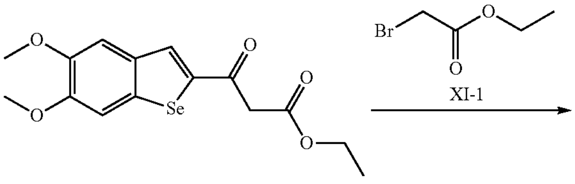
XI-1
X-1

-continued

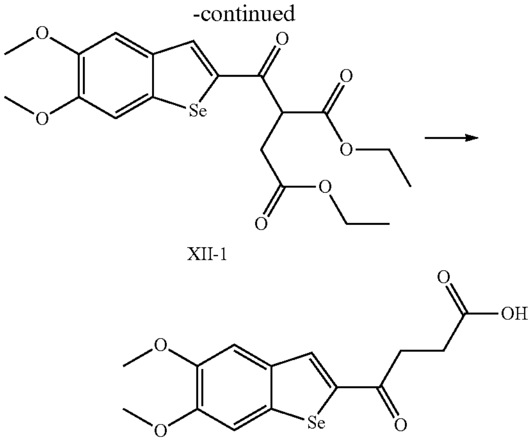

XII-1

I-1

Step 1: preparation of 2-(5,6-dimethoxybenzo[b]selenophene-2-formyl) diethyl succinate (XII-1)

0.17 g of the compound X-1 (0.5 mmol), 0.14 g of potassium carbonate (1 mmol) and 5 mL of DMF were added into a 100 mL reaction flask, and stirred for 30 mins at room temperature. 0.13 g of ethyl 2-bromoacetate (0.75 mmol) and 8 mg of potassium iodide (0.05 mmol) were added into the above reaction liquid, and continued to be stirred for 4 h at room temperature. After it was monitored by TLC that the reaction was completed, the reaction liquid was added with 20 mL of water and extracted twice using 20 mL of ethyl acetate. After being combined, organic layers were washed with water, washed with a saturated salt solution and dried with sodium sulphate anhydrous, underwent suction filtration, and were concentrated to obtain a yellow oily substance, which directly entered into the next step of the reaction without additional purification. HRMS ($ESI^+$): $C_{19}H_{23}O_7Se$ $(M+H)^+$, 443.0604; found, 443.0600.

Step 2: preparation of 4-(5,6-dimethoxybenzo[b]selenophene-2-yl)-4-oxobutanoic acid (I-1)

The compound XII-1 obtained in the previous step, 2 mL of concentrated hydrochloric acid and 2 mL of acetic acid were added into a 100 mL reaction flask, and the mixture underwent a stirred reaction at 100° C. for 3 h. After it was monitored by TLC that the reactant XII-1 reacted completely, the reaction liquid was cooled to room temperature, added with 20 mL of water for dilution, and extracted twice using 20 mL of ethyl acetate, respectively. After being combined, organic layers were washed with water, washed with a saturated salt solution and dried with sodium sulphate anhydrous, underwent suction filtration, and were concentrated to obtain a crude product. The crude product was purified by column chromatography using silica gel to obtain a white solid of 45 mg with a total yield of 26% in two steps. $^{1}$H NMR (300 MHz, DMSO-$d_6$): δ=8.42 (s, 1H), 7.70 (s, 1H), 7.53 (s, 1H), 3.84 (s, 3H), 3.82 (s, 3H), 3.24 (sbr, 2H), 2.57 (sbr, 2H) ppm. $^{13}$C NMR (75 MHz, DMSO-$d_6$): δ=193.99, 174.14, 150.77, 148.81, 145.06, 137.15, 135.46, 134.61, 109.36, 108.37, 56.24, 56.01, 32.98, 28.49 ppm. HRMS ($ESI^-$): $C_{14}H_{13}O_5Se$ $(M-H)^-$, 340.9934; found, 340.9933.

Embodiment 4

Preparation of 4-(5,6-dimethoxybenzo[b]selenophene-2-yl)-2-methyl-4-oxo-butanoic acid (I-2)

Referring to the preparation method of Embodiment 3, the compound I-2 was prepared using ethyl 2-bromopropionate instead of ethyl 2-bromoacetate by the same synthetic method. $^{1}$H NMR (300 MHz, DMSO-$d_6$): δ=12.19 (s, 1H), 8.43 (s, 1H), 7.70 (s, 1H), 7.51 (s, 1H), 3.85 (s, 3H), 3.82 (s, 3H), 3.43-3.37 (m, 1H), 3.11-3.03 (m, 1H), 2,92-2.85 (m, 1H), 1.19 (d, J=7.1 Hz, 3H) ppm. $^{3}$C NMR (75 MHz, $CDCl_3$): δ=192.78, 181.10, 150.67, 148.70, 145.30, 138.00, 135.02, 133.08, 108.21, 107.02, 56.17, 56.03, 41.25, 35.18, 17.10 ppm. HRMS ($ESI^-$): $C_{15}H_{15}O_5Se$ $(M-H)^-$, 355.0090; found, 355.0091.

Embodiment 5

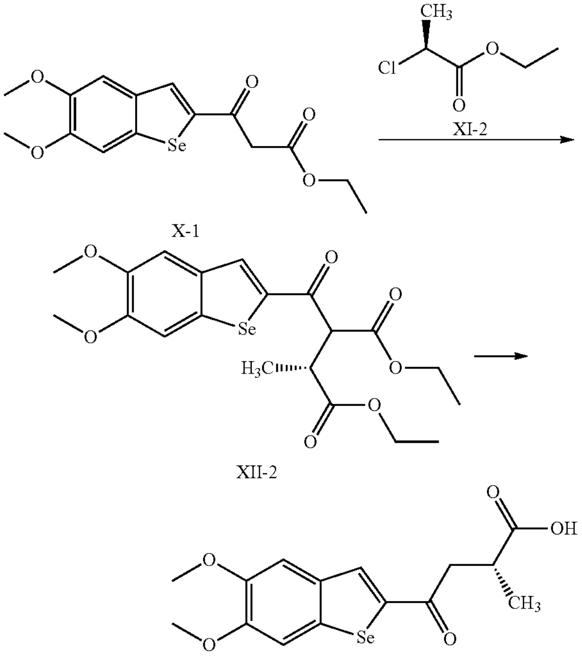

X-1

XI-2

XII-2

I-3

Step 1: preparation of (3R)-2-(5,6-dimethoxybenzo[b]selenophene-2-formoxyl)-3-diethyl methyl succinate (XII-2)

0.17 g of the compound X-1 (0.5 mmol), 0.14 g of potassium carbonate (1 mmol) and 5 mL of DMF were added into a 100 mL reaction flask, and stirred for 30 mins at room temperature. 0.14 g of ethyl(S)-2-chloropropionate (1 mmol) was added into the above reaction liquid, and stirred overnight at 55° C. The reaction was monitored by TLC. The reaction liquid was added with 20 mL of water and extracted twice using 20 mL of ethyl acetate. After being combined, organic layers were washed with water, washed with a saturated salt solution and dried with sodium sulphate anhydrous, underwent suction filtration, and were concentrated to obtain a yellow oily substance, which directly entered into the next step of the reaction without additional purification. HRMS ($ESI^+$): $C_{20}H_{25}O_7Se$ $(M+H)^+$, 457.0760; found, 457.0758.

Step 2: Preparation of R-4-(5,6-dimethoxybenzo[b] selenophene-2-yl)-2-methyl-4-oxo-butanoic acid (I-3)

The compound XII-2 obtained in the previous step, 2 mL of concentrated hydrochloric acid and 2 mL of acetic acid were added into a 100 mL reaction flask, and the mixture underwent a stirred reaction at 100° C. for 3 h. After it was monitored by TLC that the reactant XII-2 reacted completely, the reaction liquid was cooled to room temperature, added with 20 mL of water for dilution, and extracted twice using 20 mL of ethyl acetate, respectively. After being combined, organic layers were washed with water, washed with a saturated salt solution and dried with sodium sulphate anhydrous, underwent suction filtration, and were concentrated to obtain a crude product. The crude product was purified by chiral preparation to obtain a light yellow solid of 15 mg with 95% ee and a total yield of 9% in two steps. $^1H$ NMR (300 MHz, DMSO-$d_6$): δ=12.20 (s, 1H), 8.42 (s, 1H), 7.69 (s, 1H), 7.51 (s, 1H), 3.85 (s, 3H), 3.82 (s, 3H), 3.43-3.37 (m, 1H), 3.08-3.01 (m, 1H), 2.91-2.84 (m, 1H), 1.18 (d, J=7.1 Hz, 3H) ppm. $^{13}C$ NMR (75 MHz, $CDCl_3$): δ=191.59, 180.78, 151.88, 147.46, 145.55, 138.37, 134.62, 132.20, 108.17, 107.76, 56.19, 55.96, 41.19, 34.84 17.06 ppm. HRMS ($ESI^-$): $C_{15}H_{15}O_5Se$ $(M-H)^-$, 355.0090; found, 355.0088.

Embodiment 6

Preparation of S-4-(5,6-dimethoxybenzo[b]selenophene-2-yl)-2-methyl-4-oxo-butanoic acid (I-4)

Referring to the preparation method of Embodiment 5, the compound I-4 of 19 mg was prepared from a raw material of the compound X-1 using ethyl (R)-2-chloropropionate instead of ethyl (S)-2-chloropropionate by the same synthetic method with 95% ee and a total yield of 11% in two steps. $^1H$ NMR (300 MHz, DMSO-$d_6$): δ=12.12 (s, 1H), 8.42 (s, 1H), 7.70 (s, 1H), 7.51 (s, 1H), 3.85 (s, 3H), 3.82 (s, 3H), 3.43-3.37 (m, 1H), 3.09-3.02 (m, 1H), 2.91-2.85 (m, 1H), 1.19 (t, J=6.9 Hz, 3H) ppm. $^{13}C$ NMR (75 MHz, $CDCl_3$): δ=192.30, 181.22, 150.92, 147.69, 145.17, 137.61, 135.08, 133.27, 109.03, 107.21, 56.25, 56.08, 42.67, 34.44, 17.25 ppm. HRMS ($ESI^-$): $C_{15}H_{15}O_5Se$ $(M-H)^-$, 355.0090; found, 355.0089.

Embodiment 7

Preparation of 4-(5-dimethoxybenzo[b]selenophene-2-yl)-2-methyl-4-oxo-butanoic acid (I-5)

Referring to the preparation method of Embodiments 1-3, the target compound I-5 was prepared from a starting raw material of 2-bromo-5-methoxybenzaldehyde instead of 2-bromo-4,5-dimethoxybenzaldehyde, by means of a reactant of ethyl 2-bromopropionate instead of ethyl 2-bromoacetate, and by the same synthetic method. $^1H$ NMR (300 MHz, DMSO-$d_6$): δ=12.22 (s, 1H), 8.51 (s, 1H), 8.00 (d, J=8.8 Hz, 1H), 7.56 (d, J=2.6 Hz, 1H), 7.13 (dd, $J_1$=8.8 Hz, $J_2$=2.6 Hz, 1H), 3.83 (s, 3H), 3.48-3.39 (m, 1H), 3.15-3.08 (m, 1H), 2.96-2.84 (m, 1H), 1.20 (d, J=7.2 Hz, 3H) ppm. $^{13}C$ NMR (75 MHz, DMSO-$d_6$): δ=194.52, 175.23, 150.69, 146.38, 144.21, 138.17, 135.45, 133.80, 109.24, 107.26, 56.07, 42.31, 37.16, 17.47 ppm. HRMS ($ESI^-$): $C_{14}H_{13}O_4Se$ $(M-H)^-$, 324.9985; found, 324.9981.

Embodiment 8

Preparation of 4-(6-dimethoxybenzo[b]selenophene-2-yl)-2-methyl-4-oxo-butanoic acid (I-6)

Referring to the preparation method of Embodiments 1-3, the target compound I-6 was prepared from a starting raw material of 2-bromo-4-methoxybenzaldehyde instead of 2-bromo-4,5-dimethoxybenzaldehyde, by means of a reactant of ethyl 2-bromopropionate instead of ethyl 2-bromoacetate, and by the same synthetic method. $^1H$ NMR (300 MHz, DMSO-$d_6$): δ=12.19 (s, 1H), 8.50 (s, 1H), 7.92 (d, J=8.8 Hz, 1H), 7.72 (s, 1H), 7.09 (dd, $J_1$=8.8 Hz, $J_2$=2.3 Hz, 1H), 3.84 (s, 3H), 3.45-3.33 (m, 1H), 3.12-3.05 (m, 1H), 2.92-2.85 (m, 1H), 1.19 (d, J=7.2 Hz, 3H) ppm. $^3C$ NMR (75 MHz, DMSO-$d_6$): δ=193.37, 173.79, 150.51, 146.26, 143.35, 138.01, 135.14, 133.06, 110.20, 106.93, 56.15, 41.29, 35.05, 17.20 ppm. HRMS ($ESI^-$): $C_{14}H_{13}O_4Se$ $(M-H)^-$, 324.9985; found, 324.9984.

Embodiment 9

Preparation of 4-(5-hydroxyl-6-dimethoxybenzo[b] selenophene-2-yl)-2-methyl-4-oxo-butanoic acid (I-7)

Referring to the preparation method of Embodiments 1-3, the target compound I-7 was prepared from a starting raw material of 2-bromo-5-hydroxyl-4-methoxybenzaldehydeinstead of 2-bromo-4,5-dimethoxybenzaldehyde, by means of a reactant of ethyl 2-bromopropionate instead of ethyl 2-bromoacetate, and by the same synthetic method. $^1H$ NMR (300 MHz, DMSO-$d_6$): δ=12.17 (s, 1H), 9.34 (s, 1H), 8.38 (s, 1H), 7.63 (s, 1H), 7.35 (s, 1H), 3.86 (s, 3H), 3.42-3.36 (m, 1H), 3.10-3.02 (m, 1H), 2.93-2.81 (m, 1H), 1.18 (d, J=7.2 Hz, 3H) ppm. $^{13}C$ NMR (75 MHz, DMSO-$d_6$): δ=194.42, 174.41, 150.85, 149.87, 147.25, 136.47, 135.91, 133.23, 107.67, 107.05, 56.20, 42.29, 35.83, 18.93 ppm. HRMS ($ESI^-$): $C_{14}H_{13}O_5Se$ $(M-H)^-$, 340.9934; found, 340.9932.

Embodiment 10

Preparation of 2-methyl-4-oxo-4-(selenophene[2',3':4,5]benzo[1,2-d][1,3]dioxo-6-yl)butanoic acid (I-8)

Referring to the preparation method of Embodiments 1-3, the target compound I-8 was prepared from a starting raw material of 6-bromobenzo[1,2-d][1,3]dioxole-5-formaldehyde instead of 2-bromo-4,5-dimethoxybenzaldehyde, by means of a reactant of ethyl 2-bromopropionate instead of ethyl 2-bromoacetate, and by the same synthetic method. $^1H$ NMR (300 MHz, DMSO-$d_6$): δ=12.21 (s, 1H), 8.43 (s, 1H), 7.67 (s, 1H), 7.49 (s, 1H), 6.14 (s, 2H), 3.43-3.36 (m, 1H), 3.10-3.03 (m, 1H), 2.94-2.82 (m, 1H), 1.19 (d, J=7.1 Hz, 3H) ppm. $^{13}C$ NMR (75 MHz, DMSO-$d_6$): δ=193.66, 178.84, 150.75, 146.34, 144.29, 139.23, 135.11, 132.97, 109.24, 107.14, 100.42, 42.81, 34.38, 16.81 ppm. HRMS (ESI$^-$): $C_{14}H_{11}O_5Se$ (M−H)$^-$, 338.9777; found, 338.9775.

Embodiment 11

Preparation of 4-(5-ethoxy-6-dimethoxybenzo[b] selenophene-2-yl)-2-methyl-4-oxo-butanoic acid (I-9)

Referring to the preparation method of Embodiments 1-3, the target compound I-9 was prepared from a starting raw material of 2-bromo-5-ethoxy-4-methoxybenzaldehyde instead of 2-bromo-4,5-dimethoxybenzaldehyde, by means of a reactant of ethyl 2-bromopropionate instead of ethyl 2-bromoacetate, and by the same synthetic method. $^1$H NMR (300 MHz, DMSO-$d_6$): δ=12.20 (s, 1H), 8.41 (s, 1H), 7.69 (s, 1H), 7.50 (s, 1H), 4.09 (q, J=6.9 Hz, 2H), 3.85 (s, 3H), 3.43-3.37 (m, 1H), 3.10-3.03 (m, 1H), 2.92-2.85 (m, 1H), 1.40 (t, J=6.9 Hz, 3H), 1.19 (d, J=7.2 Hz, 3H) ppm. $^{13}$C NMR (75 MHz, DMSO-$d_6$): δ=193.43, 176.68, 150.50, 147.53, 144.77, 136.75, 135.07, 134.41, 109.84, 108.01, 63.82, 55.79, 40.88, 34.85, 17.10, 14.69 ppm. HRMS (ESI$^-$): $C_{16}H_{17}O_5Se$ (M−H)$^-$, 369.0247; found, 369.0244.

Embodiment 12

Preparation of 4-(5-isopropoxy-6-dimethoxybenzo [b]selenophene-2-yl)-2-methyl-4-oxo-butanoic acid (I-10)

Referring to the preparation method of Embodiments 1-3, the target compound I-10 was prepared from a starting raw material of 2-bromo-5-isopropoxy-4-methoxybenzaldehyde instead of 2-bromo-4,5-dimethoxybenzaldehyde, by means of a reactant of ethyl 2-bromopropionate instead of ethyl 2-bromoacetate, and by the same synthetic method. $^1$H NMR (300 MHz, DMSO-$d_6$): δ=12.17 (s, 1H), 8.41 (s, 1H), 7.69 (s, 1H), 7.53 (s, 1H), 4.61-4.53 (m, 1H), 3.84 (s, 3H), 3.42-3.34 (m, 1H), 3.10-3.02 (m, 1H), 2.92-2.85 (m, 1H), 1.31 (d, J=6.0 Hz, 6H), 1.19 (d, J=7.2 Hz, 3H) ppm. $^{13}$C NMR (75 MHz, DMSO-$d_6$): δ=193.87, 177.07, 151.93, 146.60, 145.18, 137.40, 135.58, 134.86, 113.04, 108.82, 71.01, 56.26, 41.32, 35.29, 22.22, 17.51 ppm. HRMS (ESI$^-$): $C_{17}H_{19}O_5Se$ (M−H)$^-$, 383.0403; found, 383.0401.

Embodiment 13

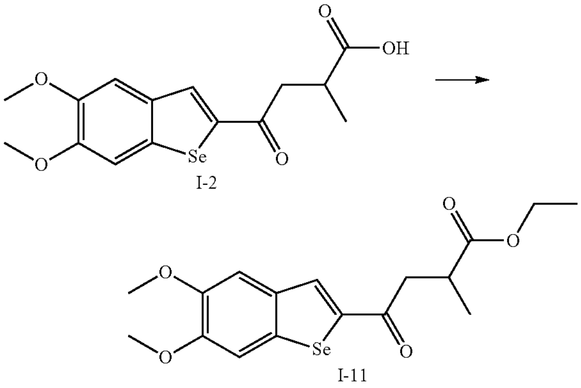

I-2

I-11

Preparation of 4-(5,6-dimethoxybenzo[b]selenophene-2-yl)-2-methyl-4-oxo-ethyl butyrate (I-11)

36 mg of the compound I-2 (0.1 mmol) was dissolved in 10 mL of ethanol, and 24 mg of thionyl chloride (0.2 mmol) was dropwise added into the reaction liquid under an ice bath. The reaction liquid was heated to flux and continued to react for 4 h. After it was detected by TLC that the reaction was completed, the reaction liquid was vaporized under reduced pressure to remove a solvent, added with 10 mL of water for dilution, and extracted twice using 10 mL of ethyl acetate. After being combined, organic layers were washed with water, washed with a saturated salt solution and dried with sodium sulphate anhydrous, underwent suction filtration, and were concentrated. A crude product was purified by column chromatography using silica gel to obtain the target compound I-11 of 34 mg with a yield of 89%. $^1$H NMR (300 MHz, DMSO-$d_6$): δ=8.43 (s, 1H), 7.70 (s, 1H), 7.51 (s, 1H), 4.08 (q, J=7.1 Hz, 2H), 3.85 (s, 3H), 3.82 (s, 3H), 3.44-3.38 (m, 1H), 3.19-3.11 (m, 1H), 2.99-2.88 (m, 1H), 1.20-1.13 (m, 6H) ppm. $^{13}$C NMR (75 MHz, DMSO-$d_6$): δ=192.97, 176.42, 151.13, 146.92, 145.19, 137.61, 135.09, 133.78, 109.95, 107.10, 62.32, 56.12, 55.81, 42.76, 35.28, 17.27, 16.84 ppm. HRMS (ESI$^+$): $C_{17}H_{21}O_5Se$ (M+H)$^+$, 385.0549; found, 385.0548.

Embodiment 14

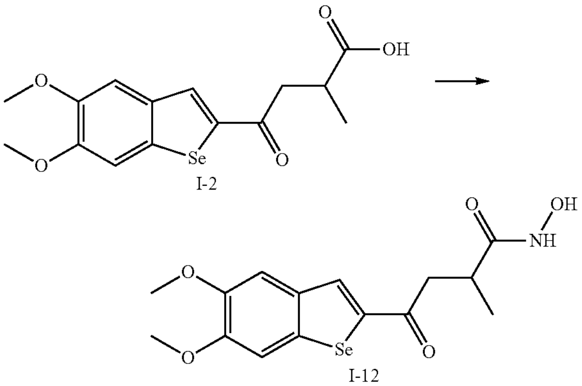

I-2

I-12

Preparation of 4-(5,6-dimethoxybenzo[b]selenophene-2-yl)-N-hydroxyl-2-methyl-4-oxo-butyramide (I-12)

177 mg of the compound I-2 (0.5 mmol) was dissolved in 10 mL of anhydrous tetrahydrofuran, 160 mg of CDI (1 mmol) was added, and the mixture was stirred for 1 h at room temperature. 69 mg of hydroxylamine hydrochloride (1 mmol) was added into the reaction liquid, and continued to be stirred overnight at room temperature. After it was detected by TLC that the reaction was completed, the reaction liquid was added with 10 mL of water for dilution, and extracted twice using 15 mL of ethyl acetate. After being combined, organic layers were washed with water, washed with a saturated salt solution and dried with sodium sulphate anhydrous, underwent suction filtration, and were concentrated. A crude product was purified by preparative TLC to obtain the target compound I-12 of 68 mg with a yield of 37%. $^1$H NMR (300 MHz, DMSO-$d_6$): δ=10.38 (s, 1H), 8.69 (s, 1H), 8.42 (s, 1H), 7.70 (s, 1H), 7.52 (s, 1H), 3.85 (s, 3H), 3.82 (s, 3H), 3.46-3.38 (m, 1H), 3.15-3.06 (m, 1H), 2,97-2.88 (m, 1H), 1.19 (d, J=7.2 Hz, 3H) ppm. $^{13}$C NMR (75 MHz, DMSO-$d_6$): δ=193.16, 175.48, 150.63, 149.07, 145.72, 137.40, 136.67, 132.81, 107.77, 107.38, 56.15, 56.01, 43.79, 36.94, 19.22 ppm. HRMS (ESI$^-$): $C_{15}H_{18}NO_5Se$ $(M-H)^-$, 370.0199; found, 370.0196.

Embodiment 15

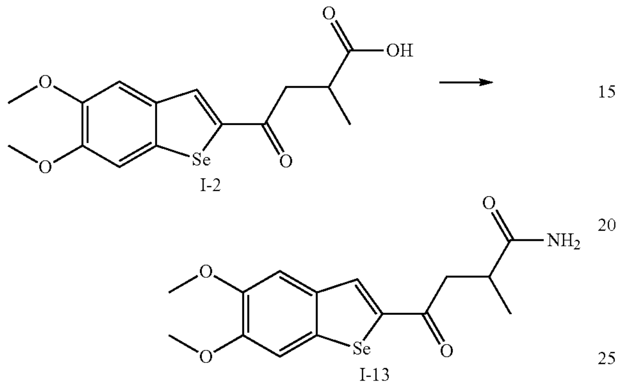

I-2

I-13

Preparation of 4-(5,6-dimethoxybenzo[b]selenophene-2-yl)-2-methyl-4-oxo-butyramide (I-13)

36 mg of the compound I-2 (0.1 mmol) and 15 mg of N-methylmorpholine (0.15 mmol) were dissolved in 10 mL of tetrahydrofuran, and 21 mg of isobutyl chloroformate (0.15 mmol) was dropwise added into the reaction liquid under an ice bath. After the completion of dropwise adding, the reaction liquid was heated to room temperature and stirred for reacting for 1 h. The reaction liquid was placed into an ice bath again, and 0.1 mL of aqueous ammonia was dropwise added. The reaction liquid reacted for 4 h at room temperature. After it was detected by TLC that the reaction was completed, the reaction liquid was added with 10 mL of water for dilution, and extracted twice using 15 mL of ethyl acetate. After being combined, organic layers were washed with water, washed with a saturated salt solution and dried with sodium sulphate anhydrous, underwent suction filtration, and were concentrated. A crude product was purified by silica gel column chromatography to obtain the target compound I-13 of 27 mg with a yield of 76%. $^1$H NMR (300 MHz, DMSO-$d_6$): δ=8.40 (s, 1H), 7.68 (s, 1H), 7.53 (s, 1H), 7.41 (s, 1H), 6.78 (s, 1H), 3.85 (s, 3H), 3.82 (s, 3H), 3.39-3.31 (m, 1H), 2.95-2.82 (m, 2H), 1.12 (d, J=6.8 Hz, 3H) ppm. $^{13}$C NMR (75 MHz, DMSO-$d_6$): δ=193.87, 176.78, 150.33, 148.36, 145.24, 136.76, 135.09, 134.24, 108.28, 107.95, 55.81, 55.59, 41.11, 35.46, 18.20 ppm. HRMS (ESI$^+$): $C_{15}H_{18}NO_4Se$ $(M+H)^+$, 356.0369; found, 356.0366.

Embodiment 16

Preparation of 4-(5,6-dimethoxybenzo[b]selenophene-2-yl)-2-ethyl-4-oxo-butanoic acid (I-14)

Referring to the preparation method of Embodiment 3, the compound I-14 was prepared from a raw material of the compound X-1 by the same synthetic method, except that ethyl 2-bromoacetate was replaced by ethyl 2-bromobutyrate. $^1$H NMR (300 MHz, DMSO-$d_6$): δ=12.19 (s, 1H), 8.45 (s, 1H), 7.70 (s, 1H), 7.51 (s, 1H), 3.85 (s, 3H), 3.82 (s, 3H), 3.43-3.37 (m, 1H), 3.11-3.04 (m, 1H), 2.82-2.73 (m, 1H), 1.66-1.56 (m, 2H), 0.95 (t, J=7.4 Hz, 3H) ppm. $^{13}$C NMR (75 MHz, $CDCl_3$): δ=192.94, 180.36, 150.71, 148.75, 145.37, 138.04, 135.06, 133.04, 108.27, 107.07, 56.19, 56.05, 41.79, 39.20, 24.95, 11.50 ppm. HRMS (ESI$^-$): $C_{16}H_{17}O_5Se$ $(M-H)^-$, 369.0247; found, 369.0246.

Embodiment 17

Preparation of R-4-(5,6-dimethoxybenzo[b]selenophene-2-yl)-2-ethyl-4-oxo-butanoic acid (I-15)

Referring to the preparation method of Embodiment 5, the target compound I-15 with 95% ee was prepared from a raw material of the compound X-1 by the same synthetic method, except that ethyl (S)-2-chloropropionate was replaced by ethyl (S)-2-chlorobutyrate as a reactant. $^1$H NMR (300 MHz, DMSO-$d_6$): δ=12.20 (s, 1H), 8.43 (s, 1H), 7.69 (s, 1H), 7.52 (s, 1H), 3.4 (s, 3H), 3.83 (s, 3H), 3.42-3.36 (m, 1H), 3.10-3.04 (m, 1H), 2.83-2.74 (m, 1H), 1.67-1.56 (m, 2H), 0.97 (t, J=7.5 Hz, 3H) ppm. $^3$C NMR (75 MHz, $CDCl_3$): δ=193.34, 180.67, 151.50, 149.27, 144.99, 138.72, 135.18, 132.03, 108.60, 107.63, 57.23, 56.11, 41.59, 38.81, 25.39, 11.05 ppm. HRMS (ESI$^-$): $C_{16}H_{17}O_5Se$ $(M-H)^-$, 369.0247; found, 369.0244.

Embodiment 18

Preparation of S-4-(5,6-dimethoxybenzo[b]selenophene-2-yl)-2-ethyl-4-oxo-butanoic acid (I-16)

Referring to the preparation method of Embodiment 5, the target compound I-16 with 95% ee was prepared from a raw material of the compound X-1 by the same synthetic method, except that ethyl (S)-2-chloropropionate was replaced by ethyl (R)-2-chlorobutyrate as a reactant. $^1$H NMR (300 MHz, DMSO-$d_6$): δ=12.19 (s, 1H), 8.44 (s, 1H), 7.69 (s, 1H), 7.52 (s, 1H), 3.85 (s, 3H), 3.83 (s, 3H), 3.43-3.35 (m, 1H), 3.13-3.02 (m, 1H), 2.83-2.75 (m, 1H), 1.66-1.55 (m, 2H), 0.95 (t, J=7.4 Hz, 3H) ppm. $^{13}$C NMR (75 MHz, $CDCl_3$): δ=192.24, 181.62, 151.74, 148.57, 144.55, 137.85, 136.49, 133.13, 109.40, 107.23, 56.17, 55.99, 42.28, 39.79, 25.01, 11.84 ppm. HRMS (ESI$^-$): $C_{16}H_{17}O_5Se$ $(M-H)^-$, 369.0247; found, 369.0246.

Embodiment 19

Preparation of 4-(5,6-dimethoxybenzo[b]selenophene-2-yl)-2-isopropyl-4-oxo-butanoic acid (I-17)

Referring to the preparation method of Embodiment 3, the compound I-17 with 95% ee was prepared from a raw material of the compound X-1 by the same synthetic method, except that ethyl 2-bromoacetate was replaced by ethyl 2-bromopropionate as a reactant. $^1$H NMR (300 MHz, $CDCl_3$): δ=8.13 (s, 1H), 7.32 (s, 1H), 7.29 (s, 1H), 3.97 (s, 3H), 3.94 (s, 3H), 3.52-3.43 (m, 1H), 3.06-3.00 (m, 2H), 2.17-2.11 (m, 1H), 1.05 (dd, $J_1$=6.8 Hz, $J_2$=2.6 Hz, 6H) ppm. $^{13}$C NMR (75 MHz, DMSO-$d_6$): δ=192.98, 180.89, 150.86, 149.61, 145.85, 138.32, 134.69, 132.20, 108.11, 106.90, 56.25, 56.07, 48.72, 40.68, 25.81, 22.57 ppm. HRMS (ESI$^-$): $C_{17}H_{19}O_5Se$ $(M-H)^-$, 383.0403; found, 383.0401.

Embodiment 20

Preparation of 2-cyclopropyl-4-(5,6-dimethoxy-benzo[b]selenophene-2-yl)-4-oxo-butanoic acid (I-18)

Referring to the preparation method of Embodiment 3, the compound I-18 was prepared from a raw material of the compound X-1 by the same synthetic method, except that ethyl 2-bromoacetate was replaced by ethyl 2-bromo-2-cyclopropylacetate. $^{1}$H NMR (300 MHz, $CDCl_3$): δ=8.28 (s, 1H), 7.35 (s, 1H), 7.31 (s, 1H), 3.98 (s, 3H), 3.96 (s, 3H), 3.50-3.41 (m, 1H), 3.10-3.02 (m, 2H), 1.12-1.04 (m, 1H), 0.57-0.49 (m, 2H), 0.21-0.14 (m, 2H) ppm. $^{3}$C NMR (75 MHz, DMSO-$d_6$): δ=194.07, 176.11, 149.78, 147.75 146.69, 138.73, 135.03, 133.12, 107.38, 107.55, 56.10, 55.74, 47.71, 40.95, 5.10 ppm. HRMS (ESI$^-$): $C_{17}H_{17}O_5Se$ $(M-H)^-$, 381.0247; found, 381.0245.

Embodiment 21

Preparation of 4-(5,6-dimethoxybenzo[b]selenophene-2-yl)-2-(methoxymethyl)-4-oxo-butanoic acid (I-19)

Referring to the preparation method of Embodiment 3, the compound I-19 was prepared from a raw material of the compound X-1 by the same synthetic method, except that ethyl 2-bromoacetate was replaced by methyl 2-bromo-3-methoxypropionate. $^{1}$H NMR (300 MHz, DMSO-$d_6$): δ=12.34 (s, 1H), 8.44 (s, 1H), 7.69 (s, 1H), 7.53 (s, 1H), 3.85 (s, 3H), 3.82 (s, 3H), 3.60-3.56 (m, 2H), 3.46-3.37 (m, 1H), 3.25 (s, 3H), 3.14-3.07 (m, 2H) ppm. $^{13}$C NMR (75 MHz, DMSO-$d_6$): δ=192.87, 179.61, 150.43, 149.39, 144.87, 138.76, 134.66, 134.09, 108.16, 107.55, 80.16, 60.98, 56.30, 56.08, 39.62, 39.04 ppm. HRMS (ESI$^-$): $C_{16}H_{17}O_6Se$ $(M-H)^-$, 385.0196; found, 385.0195.

Embodiment 22

Preparation of 2-(2-(5,6-dimethoxybenzo[b]selenophene-2-yl)-2-oxo-ethyl) hexanoic acid (I-20)

Referring to the preparation method of Embodiment 3, the compound I-20 was prepared from a raw material of the compound X-1 by the same synthetic method, except that ethyl 2-bromoacetate was replaced by ethyl 2-bromo-hexanoate. $^{1}$H NMR (300 MHz, $CDCl_3$): δ=8.10 (s, 1H), 7.32 (s, 1H), 7.28 (s, 1H), 3.97 (s, 3H), 3.94 (s, 3H), 3.49-3.39 (m, 1H), 3.13-3.07 (m, 2H), 1.80-1.57 (m, 2H), 1.37-1.32 (m, 4H), 0.93 (t, J=6.7 Hz, 3H) ppm. $^{3}$C NMR (75 MHz, DMSO-$d_6$): δ=193.85, 179.54, 150.62, 147.88, 145.47, 138.62, 136.00, 132.97, 108.83, 107.06, 56.24, 56.05, 43.93, 42.73, 35.03, 30.10, 24.75, 14.48 ppm. HRMS (ESI$^-$): $C_{18}H_{21}O_5Se$ $(M-H)^-$, 397.0560; found, 397.0558.

Embodiment 23

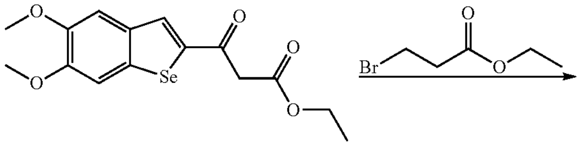

X-1

-continued

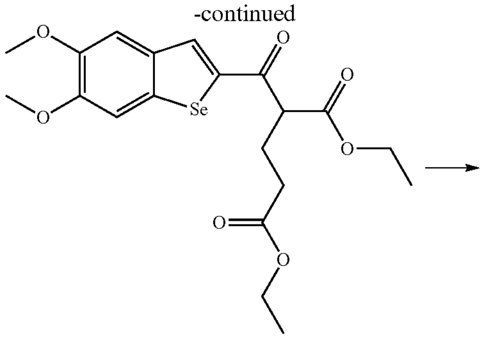

XII-3

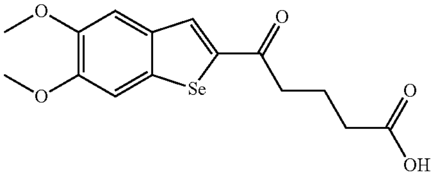

I-21

Step 1: preparation of 2-(5,6-dimethoxybenzo[b]selenophene-2-formyl) diethyl glutarate (XII-3)

0.17 g of the compound X-1 (0.5 mmol), 0.14 g of potassium carbonate (1 mmol) and 5 mL of DMF were added into a 100 mL reaction flask, and stirred for 30 mins at room temperature. 0.14 g of ethyl 3-bromopropionate (0.75 mmol) and 8 mg of potassium iodide (0.05 mmol) were added into the above reaction liquid, and the mixture underwent a stirred reaction at 55° C. for 8 h. After it was monitored by TLC that the reaction was completed, the reaction liquid was added with 20 mL of water and extracted twice using 20 mL of ethyl acetate. After being combined, organic layers were washed with water, washed with a saturated salt solution and dried with sodium sulphate anhydrous, underwent suction filtration, and were concentrated to obtain a yellow oily substance, which directly entered into the next step of the reaction without additional purification. HRMS (ESI$^+$): $C_{20}H_{25}O_7Se$ $(M+H)^+$, 457.0760; found, 457.0757

Step 2: Preparation of 5-(5,6-dimethoxybenzo[b]selenophene-2-yl)-5-oxo-pentanoic acid (I-21)

The compound XII-3 obtained in the previous step, 2 mL of concentrated hydrochloric acid and 2 mL of acetic acid were added into a 100 mL reaction flask, and the mixture was stirred for reacting at 100° C. for 3 h. After it was monitored by TLC that the reactant XII-3 reacted completely, the reaction liquid was cooled to room temperature, added with 20 mL of water for dilution, and extracted twice using 20 mL of ethyl acetate, respectively. After being combined, organic layers were washed with water, washed with a saturated salt solution and dried with sodium sulphate anhydrous, underwent suction filtration, and were concentrated to obtain a crude product. The crude product was purified by column chromatography using silica gel to obtain a white solid of 65 mg with a total yield of 37% in two steps. H NMR (300 MHz, DMSO-$d_6$): δ=12.01 (s, 1H), 8.38 (s, 1H), 7.69 (s, 1H), 7.51 (s, 1H), 3.85 (s, 3H), 3.82 (s, 3H), 3.07 (t, J=7.4 Hz, 2H), 2.34 (t, J=7.5 Hz, 2H), 1.88 (t, J=7.1 Hz, 2H) ppm. $^{13}$C NMR (75 MHz, DMSO-$d_6$): δ=193.29, 178.96, 150.56, 148.61, 146.46, 137.80, 136.19, 134.02, 109.54, 108.49, 56.25, 55.98, 42.97, 31.17, 18.41 ppm. HRMS ($ESI^-$): $C_{15}H_{15}O_5Se$ $(M-H)^-$, 355.0090; found, 355.0088.

Embodiment 24

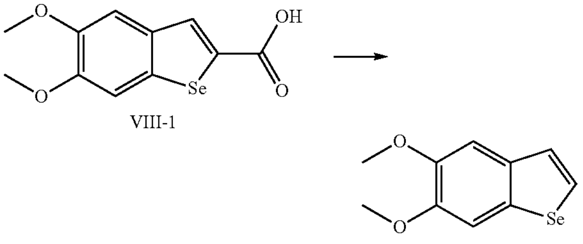

VIII-1

XIII-1

Preparation of 5,6-dimethoxybenzo[b]selenopheneformic acid (XIII-1)

0.86 g of the compound VIII-1 (3 mmol), 0.96 g of 200-mesh copper powder (15 mmol) and 12 mL of quinoline were added into a 100 mL reaction flask, and underwent a reflux reaction for 4 h. After it was monitored by TLC that the reaction was completed, suction filtration was carried out, a filtrate was taken to be added with 20 mL of 6 N hydrochloric acid, stirred for 10 mins at room temperature, and extracted twice using 30 mL of ethyl acetate. After being combined, organic layers were washed with water, washed with a saturated salt solution and dried with sodium sulphate anhydrous, underwent suction filtration, and were concentrated to obtain a crude product. The crude product was purified by column chromatography using silica gel to obtain the compound, i.e. a white solid of 0.59 g, the yield being 81%. $^1H$ NMR (300 MHz, DMSO-$d_6$): δ=7.54 (s, 1H), 7.52 (d, J=5.3 Hz, 1H), 7.37 (s, 1H), 7.29 (d, J=5.3 Hz, 1H), 3.81 (s, 3H), 3.80 (s, 3H) ppm.

Embodiment 25

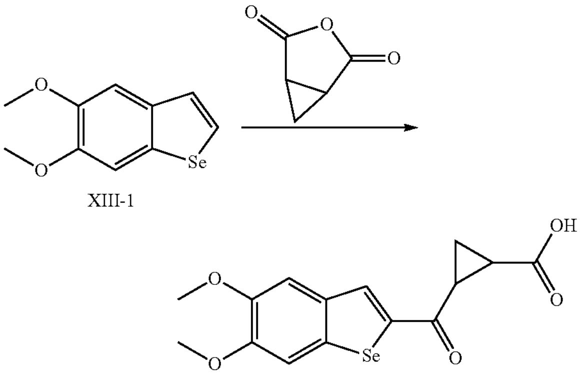

XIII-1

I-22

Preparation of 2-(5,6-dimethoxybenzo[b]selenophene-2-formyl)) cyclopropane-1-formic acid (I-22)

0.24 g of the compound (1 mmol), 0.28 g of 3-oxabicyclo [3.1.0]hexane-2,4-dione (2.5 mmol) and 5 mL of dichloromethane were added into a 100 mL reaction flask, and stirred at 0° C. for 1 h. 0.2 g of aluminum trichloride (1.5 mmol) was added into the reaction liquid, and stirred overnight at room temperature. After it was monitored by TLC that the reaction was completed, the reaction liquid was added with 10 mL of 1 N hydrochloric acid and extracted twice using 20 mL of ethyl acetate. After being combined, organic layers were washed with water, washed with a saturated salt solution and dried with sodium sulphate anhydrous, underwent suction filtration, and were concentrated to obtain a crude product. The crude product was purified by column chromatography using silica gel to obtain the compound I-22, i.e. a light yellow solid of 102 mg, the yield being 29%. 1H NMR (300 MHz, DMSO-$d_6$): δ=12.24 (s, 1H), 8.45 (s, 1H), 7.69 (s, 1H), 7.55 (s, 1H), 3.85 (s, 3H), 3.83 (s, 3H), 3.07 (q, J=8.4 Hz, 1H), 2.30 (q, J=8.0 Hz, 1H), 2.17-2.01 (m, 1H), 1.56-1.50 (m, 1H) ppm. $^{13}C$ NMR (75 MHz, $CDCl_3$): δ=194.01, 176.93, 150.61, 147.58, 145.89, 138.82, 135.66, 131.91, 108.20, 107.44, 56.30, 56.11, 27.92, 19.82, 11.53 ppm. HRMS ($ESI^-$): $C_{15}H_{13}O_5Se$ $(M-H)^-$, 352.9934; found, 352.9931.

Embodiment 26

Preparation of 2-(5,6-dimethoxybenzo[b]selenophene-2-formyl) cyclopropane-1-formic acid (I-23)

Referring to the preparation method of Embodiment 25, the target compound I-23, i.e. a light yellow solid of 58 mg, was prepared from a raw material of the compound XIII-1 by the same synthetic method, except that 3-oxabicyclo [3.1.0]hexane-2,4-dione was replaced by cyclobutane-1,4-dicarboxylic anhydride as a reactant, the yield being 32%. $^1H$ NMR (300 MHz, $CDCl_3$): δ=7.92 (s, 1H), 7.31 (s, 1H), 4.32-4.24 (m, 1H), 3.96 (s, 3H), 3.93 (s, 3H), 3.58-3.50 (m, 1H), 2.54-2.44 (m, 2H), 2.41-2.26 (m, 2H) ppm. $^{13}C$ NMR (75 MHz, $CDCl_3$): δ=193.91, 177.88, 150.59, 148.67, 144.65, 138.01, 135.06, 132.57, 108.26, 107.07, 56.19, 56.04, 44.40, 40.79, 23.13, 22.27 ppm. HRMS ($ESI^-$): $C_{16}H_{15}O_5Se$ $(M-H)^-$, 367.0090; found, 367.0089.

Embodiment 27

Preparation of 2-(5,6-dimethoxybenzo[b]selenophene-2-formyl) cyclopropane-1-formic acid (I-24)

Referring to the preparation method of Embodiment 25, the target compound I-24, i.e. a light yellow solid of 37 mg, was prepared from a raw material of the compound XIII-1 by the same synthetic method, except that 3-oxabicyclo [3.1.0]hexane-2,4-dione was replaced by 1,2-cyclohexanedicarboxylic anhydride as a reactant, the yield being 19%. $^1H$ NMR (300 MHz, DMSO-$d_6$): δ=12.20 (s, 1H), 8.44 (s, 1H), 7.70 (s, 1H), 7.55 (s, 1H), 3.85 (s, 3H), 3.83 (s, 3H), 2.66-2.60 (m, 1H), 2.58-2.53 (m, 1H), 1.85-1.56 (m, 4H), 1.49-1.30 (m, 4H) ppm. $^{13}C$ NMR (75 MHz, $CDCl_3$): δ=193.76, 176.12, 150.56, 148.95, 145.01, 137.94, 135.13, 132.29, 109.16, 107.13, 56.24, 56.06, 48.22, 42.50, 26.26, 26.07, 25.87, 23.71 ppm. HRMS ($ESI^-$): $C_{18}H_{19}O_5Se$ $(M-H)^-$, 395.0403; found, 395.0400.

Embodiment 28 Luciferase Assay Based on THP1-Lucia and RAW-Lucia

THP1-dual™ (Invivogen: thpd-nfis) cells or RAW-Lucia™ (Invivogen: rawl-isg) cells were diluted using a culture medium, and 180 μL of cell suspension was sucked and inoculated in a 96-well plate, such that each well contain $1\times10^5$ cells. 20 μL of a compound to be tested was added into the 96-well plate (the final concentration of said compound was 10 μL, and the final volume of each well was 200 L) and cultured at 37° C. for 24 h. 10 μL of supernatant was sucked into a new 96-well white plate, and 50 μL of a QUANT-Luc reagent was added. After full and even mixing, a microplate reader was used immediately for determination. There were three repeated wells set in the assay. The test result was represented as agitation fold and calculated by (test well−blank well)/(negative well−blank well). The test result was in the following tablet, with 2',3'-cGAMP as a positive control, where * represented an agitation fold of 20 or more,  represented an agitation fold of 10 to 20, and * represented an agitation fold of 1 to 10.

TABLE 1

Agitation activity of representative compounds of present invention in luciferase assay

| Code | THP1-dual | RAW-Lucia |
|---|---|---|
| I-1 | *** | *** |
| I-2 | *** | *** |
| I-3 | *** | *** |
| I-4 | *** | *** |
| I-5 | * | * |
| I-6 | * | * |
| I-7 | ** | * |
| I-8 | * | * |
| I-9 | ** | ** |
| I-10 | ** | ** |
| I-11 | * | ** |
| I-12 | * | * |
| I-13 | * | * |
| I-14 | *** | *** |
| I-15 | *** | *** |
| I-16 | *** | *** |
| I-17 | *** | ** |
| I-18 | *** | ** |
| I-19 | ** | ** |
| I-20 | ** | ** |
| I-21 | * | * |
| I-22 | ** | ** |
| I-23 | *** | *** |
| I-24 | ** | ** |

As can be seen from Table 1, the compounds of the present invention have good agitation activity on a cGAS-STING pathway.

Embodiment 29 Interferon β Induction Assay Based on THP1 Cells

Secreted cytokine IFNβ was determined by ELISA. THP1 cells were inoculated in a 96-well plate (there was no serum contained in an RPMI 1640 medium), such that the number of cells in each well ranged from $5\times10^5$ to $7\times10^5$. A DMSO stock solution of 10 mM was prepared from a compound to be tested, diluted with a culture medium to a target concentration to be added into the 96-well plate containing cells (the final concentration of said compound was 20 μM, and the final volume of each well was 200 μL), and cultured at 37° C. in 5% $CO_2$ for 3.5 h. The cells were collected at 4° C. and centrifuged at 1,000 rpm for 20 mins, and supernate was collected for ELISA determination. There were three repeated wells set in the assay. The result was shown in the following tablet, with 2',3'-cGAMP as a positive control, where the test result was represented as a percentage of activity relative to 2',3'-cGAMP at a concentration of 20 μM.

TABLE 2

Secretion of IFNβ in THP1 cells induced by part of compounds of present invention

| Code | Effect relative to 2',3'-cGAMP at 20 μM (%) |
|---|---|
| I-1 | 259 |
| I-2 | 245 |
| I-3 | 234 |
| I-4 | 201 |
| I-5 | 59 |
| I-6 | 15 |
| I-7 | 75 |
| I-8 | 20 |
| I-9 | 96 |
| I-10 | 91 |
| I-11 | 9 |
| I-12 | 11 |
| I-13 | 6 |
| I-14 | 260 |
| I-15 | 2 |
| I-16 | 281 |
| I-17 | 293 |
| I-18 | 277 |
| I-19 | 107 |
| I-20 | 132 |
| I-21 | 12 |
| I-22 | 115 |
| I-23 | 273 |
| I-24 | 142 |

As can be seen from Table 2, part of the compounds of the present invention have good activity on inducing THP1 to secrete IFNβ.

Embodiment 30 Evaluation on ADMET Properties of Part of Compounds of Present Invention The ADMET properties of part of preferable compounds were evaluated in this embodiment, and included water solubility, LogP, stability of rat liver microsome within 2 h, stability of human plasma within 24 h, THP1 cell growth inhibition activity and prediction of membrane permeation. The test result was shown in the following table, with MSA2 (Science. 2020, 369, eaba6098) as a reference compound.

TABLE 3

ADMET properties of part of compounds of present invention

| | water solubility | | | RLM | hPlasma | THP1 | Predict |
|---|---|---|---|---|---|---|---|
| Code | Water (ug/mL) | PBS (mg/mL) | LogP | @ 2 h (%) | @ 24 h (%) | $IC_{50}$ (uM) | Mem. Perm. ($10^{-6}$) |
| I-1 | 36 | 1.9 | 2.5 | >90 | >90 | >100 | 6.8 |
| I-2 | 30 | 1.0 | 2.4 | >90 | >90 | >100 | 5.9 |

TABLE 3-continued

ADMET properties of part of compounds of present invention

| Code | water solubility Water (ug/mL) | PBS (mg/mL) | LogP | RLM @ 2 h (%) | hPlasma @ 24 h (%) | THP1 $IC_{50}$ (uM) | Predict Mem. Perm. ($10^{-6}$) |
|---|---|---|---|---|---|---|---|
| I-14 | 28 | 0.7 | 2.7 | >90 | >90 | >100 | 5.3 |
| MSA2 | 6 | 0.4 | 1.5 | >90 | >90 | >100 | 5.0 |

As can be seen from Table 3, the representative compounds of the present invention have good ADMET properties.

What is claimed is:

1. A compound as shown in general formula (I-a), a stereoisomer or a pharmaceutically acceptable salt thereof:

(I-a)

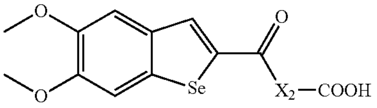

where $X^2$ is $CHR^7CHR^7$;

$R^7$ is identical or different, and each $R^7$ is independently selected from H, halo, CN, $C_1$-$C_6$ alkyl, $C_1$-$C_6$ haloalkyl, $C_1$-$C_6$ alkyl substituted with $OR^6$ and $C_3$-$C_6$ cycloalkyl; or two $R^7$ on different carbon atoms, together with atoms to which they are attached, form a 3- to 6-membered ring; and $R^6$ is independently selected from H, $C_1$-$C_3$ alkyl, $C_1$-$C_3$ haloalkyl, $C_3$-$C_6$ cycloalkyl, $C_3$-$C_8$ heterocyclyl or $C_5$-$C_{10}$ aryl.

2. A compound selected from the following formulas, stereoisomers or pharmaceutically acceptable salts thereof:

| Code | Structural formula |
|---|---|
| I-1 | 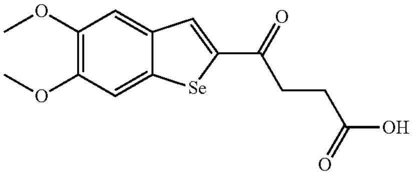 [SMILES: COc1cc2cc(C(=O)CCC(=O)O)[se]c2cc1OC] |
| I-2 | 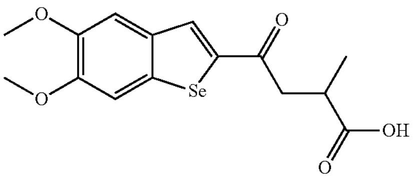 [SMILES: COc1cc2cc(C(=O)CC(C)C(=O)O)[se]c2cc1OC] |
| I-3 | 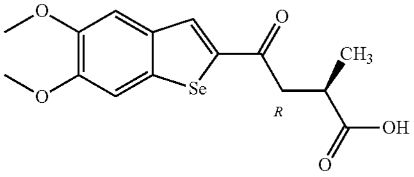 |

-continued

| Code | Structural formula |
|---|---|
| I-4 | 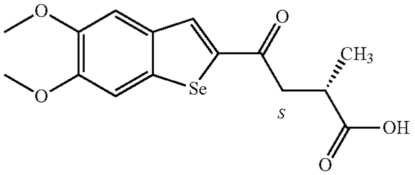 |
| I-5 | 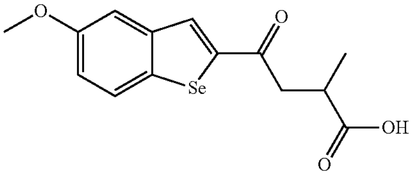 [SMILES: COc1ccc2[se]c(C(=O)CC(C)C(=O)O)cc2c1] |
| I-6 | 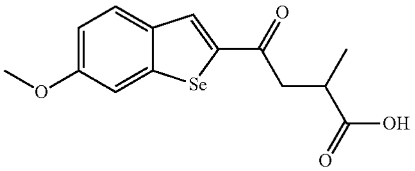 [SMILES: COc1ccc2cc(C(=O)CC(C)C(=O)O)[se]c2c1] |
| I-7 | 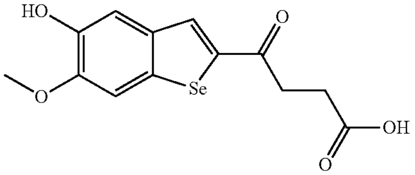 [SMILES: COc1cc2[se]c(C(=O)CCC(=O)O)cc2cc1O] |
| I-8 | 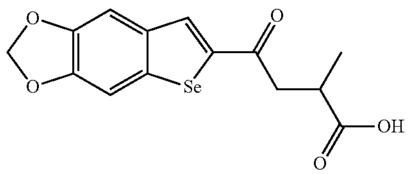 [SMILES: CC(CC(=O)c1cc2cc3c(cc2[se]1)OCO3)C(=O)O] |
| I-9 | 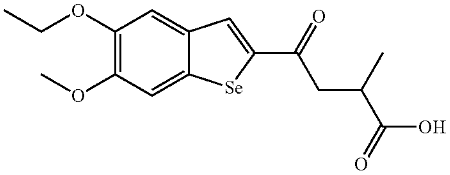 [SMILES: CCOc1cc2cc(C(=O)CC(C)C(=O)O)[se]c2cc1OC] |

-continued

| Code | Structural formula |
| --- | --- |
| I-10 | 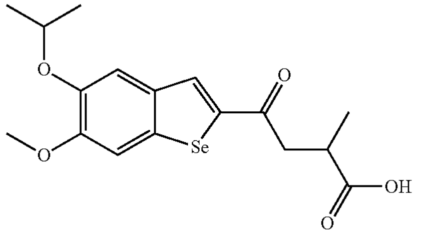 [SMILES: COc1cc2[se]c(C(=O)CC(C)C(=O)O)cc2cc1OC(C)C] |
| I-11 | 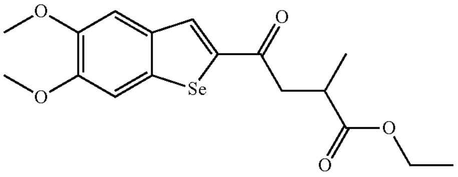 [SMILES: CCOC(=O)C(C)CC(=O)c1cc2cc(OC)c(OC)cc2[se]1] |
| I-12 | 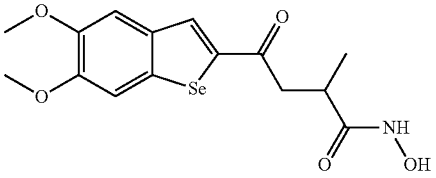 [SMILES: COc1cc2cc(C(=O)CC(C)C(=O)NO)[se]c2cc1OC] |
| I-13 | 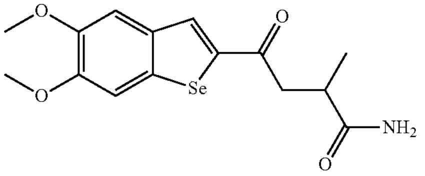 [SMILES: COc1cc2cc(C(=O)CC(C)C(N)=O)[se]c2cc1OC] |
| I-14 | 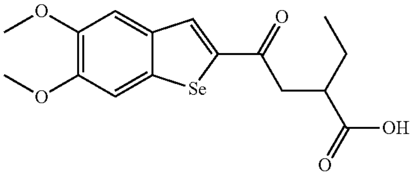 [SMILES: CCC(CC(=O)c1cc2cc(OC)c(OC)cc2[se]1)C(=O)O] |
| I-15 | 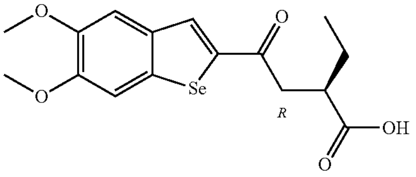 |
| I-16 | 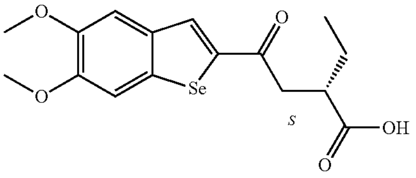 |
| I-17 | 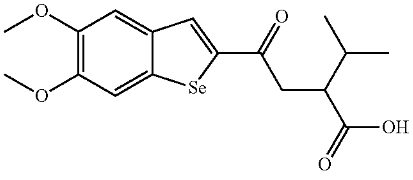 [SMILES: COc1cc2cc(C(=O)CC(C(=O)O)C(C)C)[se]c2cc1OC] |

-continued

| Code | Structural formula |
| --- | --- |
| I-18 | 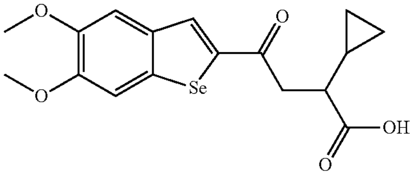 [SMILES: COc1cc2cc(C(=O)CC(C(=O)O)C3CC3)[se]c2cc1OC] |
| I-19 | 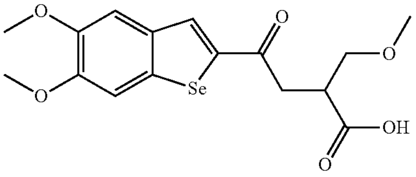 |
| I-20 | 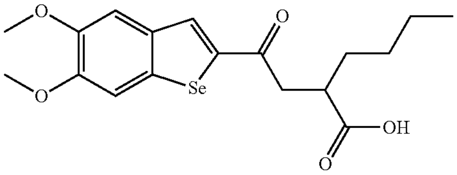 [SMILES: CCCCC(CC(=O)c1cc2cc(OC)c(OC)cc2[se]1)C(=O)O] |
| I-21 | 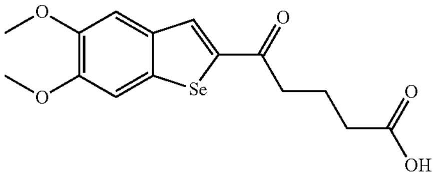 [SMILES: COc1cc2cc(C(=O)CCCC(=O)O)[se]c2cc1OC] |
| I-22 | 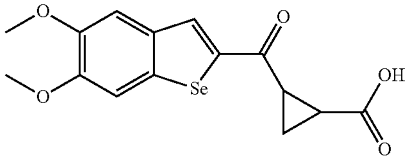 [SMILES: COc1cc2cc(C(=O)C3CC3C(=O)O)[se]c2cc1OC] |
| I-23 | 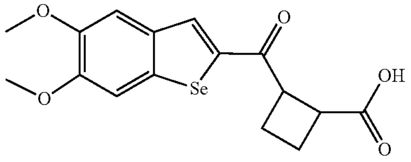 [SMILES: COc1cc2cc(C(=O)C3CCC3C(=O)O)[se]c2cc1OC] |
| I-24 | 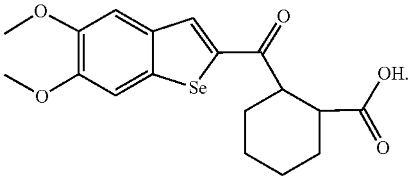 [SMILES: COc1cc2cc(C(=O)C3CCCCC3C(=O)O)[se]c2cc1OC] |

3. A drug composition comprising an active component and a pharmaceutically acceptable accessory; wherein the active component comprises a pharmaceutically effective amount of a compound, or a stereoisomer thereof or one or more of pharmaceutically acceptable salts thereof, wherein the compound is shown in general formula (I):

(I)

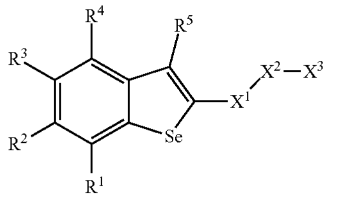

where $R^1$ is selected from H, halo, cyano, nitro, $OR^6$, $N(R^6)_2$, $C_1$-$C_6$ alkyl, $C_1$-$C_6$ haloalkyl, $C_1$-$C_6$ alkyl substituted with $OR^6$ or $C_1$-$C_6$ alkyl substituted with $N(R^6)_2$;

$R^2$ is selected from halo, cyano, nitro, $OR^6$, $SR^6$, $N(R^6)_2$, $COOR^6$, $C(O)N(R^6)_2$, $C_1$-$C_6$ alkyl, $C_1$-$C_6$ haloalkyl, $C_1$-$C_6$ alkyl substituted with $OR^6$, $C_1$-$C_6$ alkyl substituted with $N(R^6)_2$, $C_2$-$C_6$ alkenyl, $C_2$-$C_6$ haloalkenyl, $C_2$-$C_6$ alkynyl, $C_2$-$C_6$ haloalkynyl(enyl) or $C_3$-$C_6$ cycloalkyl;

$R^3$ is selected from halo, cyano, nitro, $OR^6$, $SR^6$, $N(R^6)_2$, $COOR^6$, $C(O)N(R^6)_2$, $C_1$-$C_6$ alkyl, $C_1$-$C_6$ haloalkyl, $C_1$-$C_6$ alkyl substituted with $OR^6$, and $C_1$-$C_6$ alkyl substituted with $N(R^6)_2$, $C_2$-$C_6$ alkenyl, $C_2$-$C_6$ haloalkenyl, $C_2$-$C_6$ alkynyl, $C_2$-$C_6$ haloalkynyl(enyl) or $C_3$-$C_6$ cycloalkyl;

or $R^2$ and $R^3$, together with atoms to which they are attached, can form a 5- or 6-membered heterocycle comprising one to two members selected from O, S or N ring members, $R^4$ is selected from H, halo, cyano, nitro, $OR^6$, $N(R^6)_2$, $C_1$-$C_6$ alkyl, $C_1$-$C_6$ haloalkyl, $C_1$-$C_6$ alkyl substituted with $OR^6$ or $C_1$-$C_6$ alkyl substituted with $N(R^6)_2$;

$R^5$ is selected from H, halo, cyano, $C_1$-$C_6$ alkyl, $C_1$-$C_6$ haloalkyl and $C_3$-$C_6$ cycloalkyl;

$R^6$ on the same atom is identical or different, $R^6$ on different atoms are identical or different, and each $R^6$ is independently selected from H, $C_1$-$C_6$ alkyl, $C_1$-$C_6$ haloalkyl, $C_3$-$C_6$ cycloalkyl, $C_3$-$C_8$ heterocyclyl or $C_5$-$C_{10}$ aryl;

$X^1$ is C(O);

$X^2$ is $(C(R^7)_2)_{(1-3)}$;

$R^7$ on the same atom is identical or different, $R^7$ on different atoms are identical or different, and each $R^7$ is independently selected from H, halo, CN, $OR^6$, $N(R^6)_2$, $C_1$-$C_6$ alkyl, $C_1$-$C_6$ haloalkyl, $C_1$-$C_6$ alkyl substituted with $OR^6$ or $C_3$-$C_6$ cycloalkyl;

or two $R^7$ on different carbon atoms, together with atoms to which they are attached, can form a 3- to 6-membered ring;

or two $R^7$ on a single carbon atom, together with atoms to which they are attached, can form a 3- to 6-membered ring; and $X^3$ is selected from $COOR^6$, $C(O)N(R^6)_2$, C(O)NHOH, $SO_2R^6$, $S(O)NR^6$ or $C(CF_3)_2OR^6$.

4. A preparation method for a compound, the compound being one having general formula (Ia) or one having general formula (Ib), wherein the compound of general formula (Ia) is prepared as follows: a compound of general formula (IV) is prepared from a compound of general formula (II) and compound of general formula (III) under an alkaline condition by means of a substitution reaction, a compound of general formula (VI) is prepared from the compound of general formula (IV) and a compound of general formula (V) by means of a substitution reaction, a compound of general formula (VII) is prepared from the compound of general formula (VI) under an alkaline condition by means of an intramolecular condensation reaction, a compound of general formula (VIII) is prepared from the compound of general formula (VII) by means of a hydrolysis reaction, a compound of general formula (X) is prepared from the compound of general formula (VIII) and a compound of general formula (IX) by means of a condensation reaction, a compound of general formula (XII) is prepared from the compound of general formula (X) and a compound of general formula (XI) by means of a nucleophilic substitution reaction, and a compound of general formula (Ia) is prepared from the compound of general formula (XII) by means of a hydrolytic decarboxylation reaction, a synthetic route of the compound of general formula (Ia) being as follows:

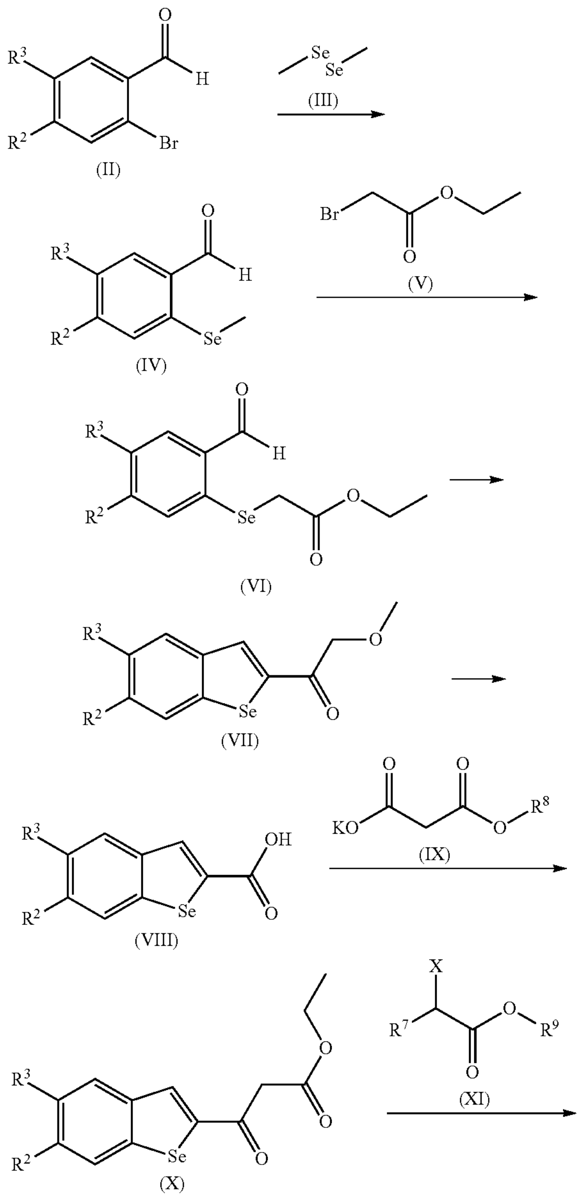

-continued

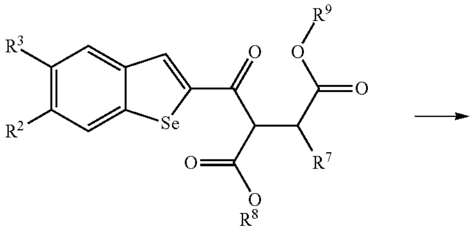

(XII)

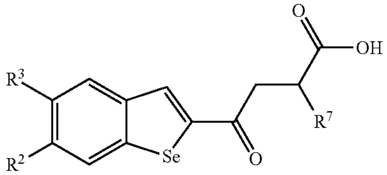

(Ia)

wherein $R^2$, $R^3$ and $R^7$ are in accordance with claim 1, $R^8$ is selected from $CH_3$, $CH_2CH_3$ and $C(CH_3)_3$, $R^9$ is selected from $CH_3$ and $CH_2CH_3$, and X is selected from Cl, Br and I;

the compound of general formula (Ib) is prepared as follows: a compound of general formula (XIII) is prepared from the compound of general formula (VIII) by means of a decarboxylic reaction, and a compound of general formula (Ib) is prepared from the compound of general formula (XIII) and a compound of general formula (XIV) by means of a Friedel-Crafts acylation, a synthetic route of the compound of general formula (XIV) being as follows:

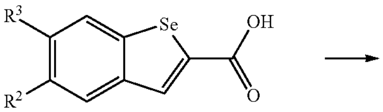

(VIII)

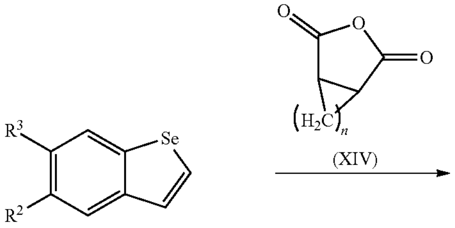

(XIV)

(XIII)

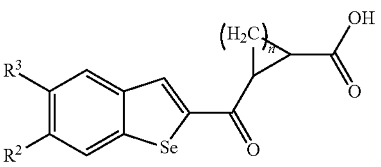

(Ib)

wherein $R^2$ and $R^3$ are in accordance with claim 1, n representing 1, 2, 3 or 4.

5. A method of activating a cGAS-STING pathway in a subject in need thereof, comprising administering a compound, a stereoisomer or a pharmaceutically acceptable salt thereof to the subject, wherein the compound is shown in general formula (I):

(I)

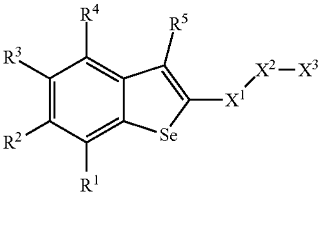

where $R^1$ is selected from H, halo, cyano, nitro, $OR^6$, $N(R^6)_2$, $C_1$-$C_6$ alkyl, $C_1$-$C_6$ haloalkyl, $C_1$-$C_6$ alkyl substituted with $OR^6$ or $C_1$-$C_6$ alkyl substituted with $N(R^6)_2$;

$R^2$ is selected from halo, cyano, nitro, $OR^6$, $SR^6$, $N(R^6)_2$, $COOR^6$, $C(O)N(R^6)_2$, $C_1$-$C_6$ alkyl, $C_1$-$C_6$ haloalkyl, $C_1$-$C_6$ alkyl substituted with $OR^6$, $C_1$-$C_6$ alkyl substituted with $N(R^6)_2$, $C_2$-$C_6$ alkenyl, $C_2$-$C_6$ haloalkenyl, $C_2$-$C_6$ alkynyl, $C_2$-$C_6$ haloalkynyl(enyl) or $C_3$-$C_6$ cycloalkyl;

$R^3$ is selected from halo, cyano, nitro, $OR^6$, $SR^6$, $N(R^6)_2$, $COOR^6$, $C(O)N(R^6)_2$, $C_1$-$C_6$ alkyl, $C_1$-$C_6$ haloalkyl, $C_1$-$C_6$ alkyl substituted with $OR^6$, and $C_1$-$C_6$ alkyl substituted with $N(R^6)_2$, $C_2$-$C_6$ alkenyl, $C_2$-$C_6$ haloalkenyl, $C_2$-$C_6$ alkynyl, $C_2$-$C_6$ haloalkynyl(enyl) or $C_3$-$C_6$ cycloalkyl;

or $R^2$ and $R^3$, together with atoms to which they are attached, can form a 5- or 6-membered heterocycle comprising one to two members selected from O, S or N ring members, $R^4$ is selected from H, halo, cyano, nitro, $OR^6$, $N(R^6)_2$, $C_1$-$C_6$ alkyl, $C_1$-$C_6$ haloalkyl, $C_1$-$C_6$ alkyl substituted with $OR^6$ or $C_1$-$C_6$ alkyl substituted with $N(R^6)_2$;

$R^5$ is selected from H, halo, cyano, $C_1$-$C_6$ alkyl, $C_1$-$C_6$ haloalkyl and $C_3$-$C_6$ cycloalkyl;

$R^6$ on the same atom is identical or different, $R^6$ on different atoms are identical or different, and each $R^6$ is independently selected from H, $C_1$-$C_6$ alkyl, $C_1$-$C_6$ haloalkyl, $C_3$-$C_6$ cycloalkyl, $C_3$-$C_8$ heterocyclyl or $C_5$-$C_{10}$ aryl;

$X^1$ is C(O);

$X^2$ is $(C(R^7)_2)_{(1-3)}$;

$R^7$ on the same atom is identical or different, $R^7$ on different atoms are identical or different, and each $R^7$ is independently selected from H, halo, CN, $OR^6$, $N(R^6)_2$, $C_1$-$C_6$ alkyl, $C_1$-$C_6$ haloalkyl, $C_1$-$C_6$ alkyl substituted with $OR^6$ or $C_3$-$C_6$ cycloalkyl;

or two $R^7$ on different carbon atoms, together with atoms to which they are attached, can form a 3- to 6-membered ring;

or two $R^7$ on a single carbon atom, together with atoms to which they are attached, can form a 3- to 6-membered ring; and $X^3$ is selected from $COOR^6$, $C(O)N(R^6)_2$, C(O)NHOH, $SO_2R^6$, $S(O)NR^6$ or $C(CF_3)_2OR^6$.

6. A method comprising administering a compound, a stereoisomer or a pharmaceutically acceptable salt thereof to a subject in need of treatment of a disease related to activity of a STING pathway, wherein the compound is shown in general formula (I):

(I)

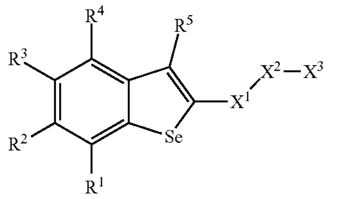

where $R^1$ is selected from H, halo, cyano, nitro, $OR^6$, $N(R^6)_2$, $C_1$-$C_6$ alkyl, $C_1$-$C_6$ haloalkyl, $C_1$-$C_6$ alkyl substituted with $OR^6$ or $C_1$-$C_6$ alkyl substituted with $N(R^6)_2$;

$R^2$ is selected from halo, cyano, nitro, $OR^6$, $SR^6$, $N(R^6)_2$, $COOR^6$, $C(O)N(R^6)_2$, $C_1$-$C_6$ alkyl, $C_1$-$C_6$ haloalkyl, $C_1$-$C_6$ alkyl substituted with $OR^6$, $C_1$-$C_6$ alkyl substituted with $N(R^6)_2$, $C_2$-$C_6$ alkenyl, $C_2$-$C_6$ haloalkenyl, $C_2$-$C_6$ alkynyl, $C_2$-$C_6$ haloalkynyl(enyl) or $C_3$-$C_6$ cycloalkyl;

$R^3$ is selected from halo, cyano, nitro, $OR^6$, $SR^6$, $N(R^6)_2$, $COOR^6$, $C(O)N(R^6)_2$, $C_1$-$C_6$ alkyl, $C_1$-$C_6$ haloalkyl, $C_1$-$C_6$ alkyl substituted with $OR^6$, and $C_1$-$C_6$ alkyl substituted with $N(R^6)_2$, $C_2$-$C_6$ alkenyl, $C_2$-$C_6$ haloalkenyl, $C_2$-$C_6$ alkynyl, $C_2$-$C_6$ haloalkynyl(enyl) or $C_3$-$C_6$cycloalkyl;

or $R^2$ and $R^3$, together with atoms to which they are attached, can form a 5- or 6-membered heterocycle comprising one to two members selected from O, S or N ring members;

$R^4$ is selected from H, halo, cyano, nitro, $OR^6$, $N(R^6)_2$, $C_1$-$C_6$ alkyl, $C_1$-$C_6$ haloalkyl, $C_1$-$C_6$ alkyl substituted with $OR^6$ or $C_1$-$C_6$ alkyl substituted with $N(R^6)_2$;

$R^5$ is selected from H, halo, cyano, $C_1$-$C_6$ alkyl, $C_1$-$C_6$ haloalkyl and $C_3$-$C_6$ cycloalkyl;

$R^6$ on the same atom is identical or different, $R^6$ on different atoms are identical or different, and each $R^6$ is independently selected from H, $C_1$-$C_6$ alkyl, $C_1$-$C_6$ haloalkyl, $C_3$-$C_6$ cycloalkyl, $C_3$-$C_8$ heterocyclyl or $C_5$-$C_{10}$ aryl;

$X^1$ is C(O);

$X^2$ is $(C(R^7)_2)_{(1\text{-}3)}$;

$R^7$ on the same atom is identical or different, $R^7$ on different atoms are identical or different, and each $R^7$ is independently selected from H, halo, CN, $OR^6$, $N(R^6)_2$, $C_1$-$C_6$ alkyl, $C_1$-$C_6$ haloalkyl, $C_1$-$C_6$ alkyl substituted with $OR^6$ or $C_3$-$C_6$ cycloalkyl;

or two $R^7$ on different carbon atoms, together with atoms to which they are attached, can form a 3- to 6-membered ring;

or two $R^7$ on a single carbon atom, together with atoms to which they are attached, can form a 3- to 6-membered ring; and $X^3$ is selected from $COOR^6$, $C(O)N(R^6)_2$, C(O)NHOH, $SO_2R^6$, $S(O)NR^6$ or $C(CF_3)_2OR^6$.

* * * * *